US010471129B2

(12) United States Patent
Mahlapuu et al.

(10) Patent No.: US 10,471,129 B2
(45) **Date of Patent: *Nov. 12, 2019**

(54) HYALURONIC ACID CONTAINING COMPOSITIONS FOR PREVENTION OF THE FORMATION OF POST-SURGICAL SCARS AND POST-SURGICAL ADHESIONS

(71) Applicant: PERGAMUM AB, Solna (SE)

(72) Inventors: Margit Mahlapuu, Gothenburg (SE); Mattias Munnich, Hindås (SE); Veronika Sjostrand, Hindås (SE)

(73) Assignee: PERGAMUM AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/851,025

(22) Filed: Dec. 21, 2017

(65) Prior Publication Data

US 2018/0200341 A1 Jul. 19, 2018

Related U.S. Application Data

(60) Continuation of application No. 14/458,637, filed on Aug. 13, 2014, now Pat. No. 9,878,019, which is a division of application No. 13/143,875, filed as application No. PCT/EP2010/050284 on Jan. 12, 2010, now abandoned.

(30) Foreign Application Priority Data

Jan. 13, 2009 (SE) ...................................... 0900031

(51) Int. Cl.

| | |
|---|---|
| ***A61K 38/40*** | (2006.01) |
| ***A61K 9/00*** | (2006.01) |
| ***A61K 9/06*** | (2006.01) |
| ***A61K 31/728*** | (2006.01) |
| ***A61K 45/06*** | (2006.01) |
| ***A61K 47/36*** | (2006.01) |
| ***A61L 31/16*** | (2006.01) |
| ***A61K 38/08*** | (2019.01) |
| ***A61K 38/10*** | (2006.01) |

(52) U.S. Cl.

CPC ............ *A61K 38/40* (2013.01); *A61K 9/0014* (2013.01); *A61K 9/06* (2013.01); *A61K 31/728* (2013.01); *A61K 38/08* (2013.01); *A61K 38/10* (2013.01); *A61K 45/06* (2013.01); *A61K 47/36* (2013.01); *A61L 31/16* (2013.01); *A61L 2300/232* (2013.01); *A61L 2300/252* (2013.01)

(58) Field of Classification Search

None

See application file for complete search history.

(56) References Cited

U.S. PATENT DOCUMENTS

| | | | |
|---|---|---|---|
| 4,141,973 | A | 2/1979 | Balazs |
| 5,080,893 | A | 1/1992 | Goldberg et al. |
| 5,304,633 | A | 4/1994 | Tomita et al. |
| 6,037,331 | A | 3/2000 | Shalaby et al. |
| 6,086,907 | A | 7/2000 | Goldberg et al. |
| 7,253,143 | B1 | 8/2007 | Hanson et al. |
| 7,427,589 | B2 | 9/2008 | Olmarker |
| 9,878,019 | B2 | 1/2018 | Mahlapuu et al. |
| 2002/0132790 | A1 | 9/2002 | Benedetti et al. |
| 2003/0109422 | A1 | 6/2003 | Mazzone et al. |
| 2007/0021704 | A1 | 1/2007 | Hariri et al. |
| 2007/0104764 | A1 | 5/2007 | Jensen et al. |

FOREIGN PATENT DOCUMENTS

| | | | |
|---|---|---|---|
| EP | 0718312 | A2 | 6/1996 |
| EP | 2050461 | A1 | 4/2009 |
| WO | 9010031 | A1 | 9/1990 |
| WO | 9707833 | A2 | 3/1997 |
| WO | 0000214 | A2 | 1/2000 |
| WO | 0001730 | A1 | 1/2000 |
| WO | 0160868 | A1 | 8/2001 |
| WO | 0209792 | A1 | 2/2002 |
| WO | 0230990 | A1 | 4/2002 |
| WO | 0244276 | A2 | 6/2002 |
| WO | 2004020473 | A1 | 3/2004 |
| WO | 2005024002 | A1 | 3/2005 |
| WO | 2005089472 | A2 | 9/2005 |
| WO | 200604744 | A2 | 1/2006 |
| WO | 2006037592 | A1 | 4/2006 |
| WO | 2006047744 | A2 | 5/2006 |

OTHER PUBLICATIONS

Abdominal adhesions (retrieved from http://www.niddk.nih.gov/health-information/health-topics/digestive-disea- ses/abdominal-adhesions/Pages/facts.aspx onOct. 20, 2015, 7 pages).
Adhesions web site (retrieved from http://www.adhesions.org/ptguide.sub.-print.htm on Apr. 3, 2017, 12 pages).
Andrew Pakula et al., Genetic Analysis of Protein Stability and Function, 23 Annu. Rev. Genet. 289-310 (1989).
Beck, D.E. et al., A prospective, randomized, multicenter, controlled study of the safety of Seprafilm adhesion barrier in abdominopelvic surgery of the intestine. Dis Colon Rectum 2003; 46:1310-1319.
Beck, D.E., The role of Seprafilm bioresorbable membrane in adhesion prevention. Eur J Surg 1997; Suppl 577: 49-55.
Brown, et al., Genetic susceptibility to raised dermal scarring, 161 British Journal of Dermatology 8-18 (2009).
Cavallari, E. et al., Inability of University of Wisconsin solution to reduce postoperative peritoneal adhesions in rats. Eur J Surg 2000;166: 650-653.

(Continued)

*Primary Examiner* — Karlheinz R. Skowronek
*Assistant Examiner* — Ronald T Niebauer
(74) *Attorney, Agent, or Firm* — McCarter & English, LLP; Steven G. Davis

(57) ABSTRACT

The present invention relates to pharmaceutical compositions enhancing the therapeutic effect of biologically active peptides, especially peptides derived from human lactoferrin. The compositions are useful for the treatment and/or prevention of wounds, scars, and post surgical adhesions.

8 Claims, 4 Drawing Sheets

Specification includes a Sequence Listing.

(56) References Cited

OTHER PUBLICATIONS

Daughton et al. ('Lower-dose prescribing: Minimizing "side effects" of pharmaceuticals on society and the environment' Science of the Total Environment v443 2013 pp. 324-337).
DeCherney, A.H. et al., Clinical problem of intraperitoneal post-surgical adhesion formation following general surgery and the use of adhesion prevention barriers. Surg Clin North Am, Jun. 1997; vol. 77: 671-688.
Diamond, M.P., Reduction of adhesions after uterine myomectomy by Seprafilm membrane (HAL-F): a blinded, prospective, randomized, multicenter clinical study. Seprafilm Adhesion Study Group, Fertil Steril, Dec. 1996; vol. 66: 904-910.
Diegelmann et al., Wound Healing: An Overview of Acute, Fibrotic and Delayed Healing, 9 Frontiers in Bioscience 283-289 (Jan. 1, 2004).
DiZerega, G.S. et al., A randomized, controlled pilot study of the safety and efficacy of 4% icodextrin solution in the reduction of adhesions following laparoscopic gynaecological surgery. Hum Reprod 2002. vol. 17, No. 4: 1031-1038.
Ellis et al., Adhesion-related hospital readmissions after abdominal and pelvic surgery: a retrospective cohort study, 353 The Lancet 1476-1480 (May 1, 1999).
English translation of Japanese Office Action dated Jul. 16, 2013, in corresponding Japanese Patent Application No. 2011-544890.
Golash et al., Efficacy of Adcon-T/N. After Primary Flexor Tendon Repair in Zone II: A Controlled Clinical Trial, 28B(2) The Journal of Hand Surgery 113-115 (2003).
Hagberg et al., Sodium hyaluronate as an adjunct in adhesion prevention after flexor tendon surgery in rabbits, 17A(5) The Journal of Hand Surgery 935-941 (1992).
Hagberg, Exogenous hyaluronate as an adjunct in the prevention of adhesion after flexor tendon surgery: a controlled clinical trial, 17A(1) The Journal of Hand Surgery 132-136 (1992).
Harris et al., Analysis of the kinetics of peritoneal adhesion formation in the rat and evaluation of potential antiadhesive agents, 117(6) Surgery 663-669 (1995).
Holmdahl, L. et al., Adhesions: pathogenesis and prevention-panel discussion and summary. Eur J Surg 1997; Suppl 577:56-62.
International Preliminary Report on Patentability (PCT/IPEA/409) dated Apr. 29, 2011, by European Patent Office as the International Searching Authority for International Application No. PCT/EP2010/050284.
International Search Report (PCT/ISA/210) dated Oct. 10, 2010, by European Patent Office as the International Searching Authority for International Application No. PCT/EP2010/050284.
Kijlstra et al., Lactoferrin levels in normal human tears British Journal of Ophthalmology v67 1983 pp. 199-202).
LeGrand, E.K. et al., Comparative efficacy of nonsteroidal anti-inflammatory drugs and anti-thromboxane agents in a rabbit adhesion-prevention model. J Invest Surg 1995. vol. 8: 187-194.
Li, H. et al., Synthesis and biological evaluation of a cross-linked hyaluronan-mitomycin C hydrogel. Biomacromolecules 2004; vol. 5: 895-902.
Mais, V. et al., Prevention of de-novo adhesion formation after laparoscopic myomectomy: a randomized trial to evaluate the effectiveness of an oxidized regenerated cellulose absorbable barrier, Hum Reprod. 1995, vol. 10, No. 12: 3133-3135.
Mais, V. et al., Reduction of adhesion reformation after laparoscopic endometriosis surgery: a randomized trial with an oxidized regenerated cellulose absorbable barrier, Obstet Gynecol. 1995, vol. 86: 512-515.
Mentzel et al., The Effectiveness of Adcon-T/N , A New Anti-Adhesion Barrier Gel, in Fresh Divisions of the Flexor Tendons in Zone II, 25B(6) Journal of Hand Surgery 590-592 (2000).
Meyers et al., Effect of Hyaluronic Acid/Chondroitin Sulfate on Healing of Full-Thickness Tendon Lacerations in Rabbits, 7 Journal of Orthopaedic Research 683-689 (1989).
Necas et al., Hyaluronic acid (hyaluronan): a review Veterinar ni Medicina 53(8) 2008 pp. 397-411).
Nilsson et al., A Novel Polypeptide Derived From Human Lactoferrin in Sodium Hyaluronate Prevents Postsurgical Adhesion Formation in the Rat, 250(6) Annals of Surgery 1021-1028, Dec. 2009.
Oh et al. ('Signal transduction of hyaluronic acid-peptide conjugate for formyl peptide receptor like 1 receptor' Bioconjugate Chem. v19 2008 pp. 2401-2408).
Paves et al., Tear concentration of hyaluronic acid in normal subjects and patients with graves ophthalmopathy v47 2006 E-abstract 1965 retrieved from http:l/abstracts.iovs.org/cgi/content!abstract/47/5/1965 on Jul. 15, 2013 and printed as 2pages).
Prevent wound infection in time (retrieved from http://silvergreen.fi/wp-content/uploads/2015/04/prevent.sub.--wound.sub.- --infection.pdf on Oct. 20, 2015, 2 pages).
Price et al., Hyaluronic acid: the scientific and clinical evidence Journal of Plastic, Reconstructive, and Aesthetic Surgery v60 2007 pp. 1110-1119.
Sawada et al. ('Adhesion prevention effect on hyaluronic acid after intraperitoneal surgery in mice' Human Reproduction v14(6) 1999 pp. 1470-1472).
Severin, Biochemistry 39-45 (2003) (with English translation of p. 40).
Skin injury (retrieved from https://www.sharecare.com/health/skin-injury/how-can-i-prevent-scar on Oct. 20, 2015, 6 pages).
Tang, C-L. et al., Bioresorbable adhesion barrier facilitates early closure of the defunctioning ileostomy after rectal excision: a prospective, randomized trial. Dis Colon Rectum 2003, vol. 46: 1200-1207.
The Cleveland Clinic (retrieved from http://my.clevelandclinic.org/health/articles/scars on Apr. 3, 2017, 5 pages).
The Free Dictionary (retrieved from http://medical-dictionary.thefreedictionary.com/prevention on Apr. 3, 2017 , 4 pages).
The free dictionary entry for prophylactic (retrieved from http://medical-dictionary.thefreedictionary.com/prophylactically on Oct. 20, 2015, 3 pages).
USPTO Connection (retrieved from http://www.moazzamlaw.com/dev/Vol1-Issue2.pdf on Apr. 3, 2017, 3 pages).
Vrijland, W.W. et al., Fewer intraperitoneal adhesions with use of hyaluronic acid-carboxymethylcellulose membrane: a randomized clinical trial. Ann. Surg. 2002, vol. 235, No. 2:193-199.
Wallwiener, D. et al., Adhesion formation of the parietal and visceral peritoneum: an explanation for the controversy on the use of autologous and alloplastic barriers? Fertil Steril., Jan. 1998, vol. 68, No. 1: 132-137.
Wiig et al., PXL01 in Sodium Hyaluronate for Improvement of Hand Recovery after Flexor Tendon Repair Surgery: Randomized Controlled Trial, 9(10) Plos 1-11 (Oct. 2014).
Yaacobi, Y. et al., Effect of Ringer's lactate irrigation on the formation of postoperative abdominal adhesions. J Invest Surg 1991, vol. 4: 31-36.
Zeng et al., Efficacy and Safety of Seprafilm for Preventing Postoperative Abdominal Adhesion: Systematic Review and Meta-analysis, 31 World J Surg. 2125-2131 (2007).

C

D

E

HYALURONIC ACID CONTAINING COMPOSITIONS FOR PREVENTION OF THE FORMATION OF POST-SURGICAL SCARS AND POST-SURGICAL ADHESIONS

RELATED APPLICATIONS

This application is a Continuation Application of U.S. patent application Ser. No. 14/458,637, filed on Aug. 13, 2014, which is a Divisional Application of U.S. patent application Ser. No. 13/143,875, filed on Jul. 8, 2011. U.S. patent application Ser. No. 13/143,875 is the 35 U.S.C. § 371 national stage filing of International Application No. PCT/EP2010/050284, filed on Jan. 12, 2010, which claims priority to Swedish Patent Application No. 0900031-6, filed on Jan. 13, 2009. The entire teachings of U.S. Ser. Nos. 14/458,637 and 13/143,875 are incorporated herein by reference.

FIELD OF THE INVENTION

The present invention relates to pharmaceutical compositions enhancing the therapeutic effect of biologically active peptides, especially peptides derived from human lactoferrin. The compositions are useful for the treatment and/or prevention of wounds, scars, and post surgical adhesions.

BACKGROUND

Peritoneal adhesions are fibrous tissue connections between abdominal structures following surgical trauma or other types of injury. General abdominal, vascular, gynaecological, urological and orthopaedic surgery may lead to adhesion formation in up to 95% of patients (Ellis et al. 1999. *Adhesion-related hospital readmissions after abdominal and pelvic surgery: a retrospective cohort study.* Lancet 353, 1476-1480). Post-surgical adhesions are considered the main cause of small bowel obstruction (Menzies et al. 2001. *Small bowel obstruction due to postoperative adhesions: treatment patterns and associated costs in 110 hospital admissions.* Ann R Coll Surg Enql 83, 40-46.), a well-known aetiology of secondary infertility in females (Marana et al. 1995. *Correlation between the American Fertility Society classifications of adnexal adhesions and distal tubal occlusion, salpingoscopy, and reproductive outcome in tubal surgery.* Fertil Steril 64, 924-929) as well as a possible cause of postoperative pain (Paajanen et al. 2005. *Laparoscopy in chronic abdominal pain: a prospective nonrandomized long-term follow-up study.* J Clin Gastroenterol 39, 110-114). More than 30% of individuals undergoing lower abdominal surgery are readmitted for disorders directly or possibly related to adhesion formation at some period of their life (Lower et al. 2000. *The impact of adhesions on hospital readmissions over ten years after 8849 open gynaecological operations: an assessment from the Surgical and Clinical Adhesions Research Study.* Biog 107, 855-862.).

In many decades, attempts to reduce post-surgical adhesions by reducing surgical trauma (avoiding desiccation, gentle tissue handling, meticulous hemostasis) and contamination of the abdominal cavity with foreign materials (using starch-free gloves, lint-free gauze and absorbable sutures) have been done (Holmdahl et al. 1997. *Adhesions: pathogenesis and prevention-panel discussion and summary.* Eur J Surg Suppl, 56-62.). Importantly, the laparoscopic techniques are not sufficient to overcome the problem of postoperative adhesion formation (Duron et al. 2000. *Prevalence and mechanisms of small intestinal obstruction following laparoscopic abdominal surgery: a retrospective multicenter study.* French Association for Surgical Research. Arch Surg 135, 208-212). Thus, intra-peritoneal adhesions remain a major clinical issue and it is now believed that future improvements may only marginally be influenced through superior surgical technique. Instead, the focus is to develop dedicated products for prevention of adhesion formation, which are administrated in connection to the surgical intervention.

Most of the therapeutic strategies tested in prevention of adhesions are medical device products. Different types of physical barriers have been evaluated, where the biodegradable films applied during the intervention are used to keep the injured abdominal surfaces separated during the critical period of peritoneal healing. The two most widely used adhesion-reducing barriers are Interceed (Johnson & Johnson Medical Inc., Arlington, Tex.) and Seprafilm™ (Genzyme, Cambridge, Mass., USA). Seprafilm™, composed of sodium hyaluronic acid and carboxymethylcellulose (CMC) forms a viscous gel approximately 24-48 h after placement, which is slowly resorbed within 1 week (Diamond, 1996. *Reduction of adhesions after uterine myomectomy by Seprafilm membrane (HAL-F): a blinded, prospective, randomized, multicenter clinical study.* Seprafilm Adhesion Study Group. Fertil Steril 66, 904-910; Beck, 1997. *The role of Seprafilm bioresorbable membrane in adhesion prevention.* Eur J Surg Suppl, 49-55). Seprafilm™ has been shown to reduce post-surgical adhesion in clinical situation (Vrijland et al. 2002. *Fewer intraperitoneal adhesions with use of hyaluronic acid-carboxymethylcellulose membrane: a randomized clinical trial.* Ann Surg 235, 193-199.; Beck et al. 2003. *A prospective, randomized, multicenter, controlled study of the safety of Seprafilm adhesion barrier in abdominopelvic surgery of the intestine.* Dis Colon Rectum 46, 1310-1319; Tang et al. 2003. *Bioresorbable adhesion barrier facilitates early closure of the defunctioning ileostomy after rectal excision: a prospective, randomized trial.* Dis Colon Rectum 46, 1200-1207), however, the device is difficult to apply, as it adheres to gloves and organs and is brittle (DeCherney & diZerega, 1997. *Clinical problem of intraperitoneal postsurgical adhesion formation following general surgery and the use of adhesion prevention barriers.* Surg Clin North Am 77, 671-688). Additionally, Seprafilm™ increases the risk of sequelae associated with anastomosic leak and is not compatible with laparoscopic procedures (diZerega et al. 2002. *A randomized, controlled pilot study of the safety and efficacy of 4% icodextrin solution in the reduction of adhesions following laparoscopic gynaecological surgery.* Hum Reprod 17, 1031-1038). Interceed, composed of oxidized regenerated cellulose, is transformed into a gelatinous mass covering the injured peritoneum and has shown efficacy in adhesion-prevention in several clinical studies (Mais et al. 1995. *Prevention of de-novo adhesion formation after laparoscopic myomectomy: a randomized trial to evaluate the effectiveness of an oxidized regenerated cellulose absorbable barrier* Hum Reprod. 10, 3133-3135; Mais et al. 1995 *Reduction of adhesion reformation after laparoscopic endometriosis surgery: a randomized trial with an oxidized regenerated cellulose absorbable barrier* Obstet Gynecol. 86, 512-515; Wallwiener et al. 1998. *Adhesion formation of the parietal and visceral peritoneum: an explanation for the controversy on the use of autologous and alloplastic barriers?* Fertil Steril 69, 132-137). However, application of Interceed requires complete hemostasis as even small amounts of intraperitoneal bleeding negates any beneficial effect of this barrier (DeCherney & diZerega, 1997. supra). A general limitation of using the physical barriers is the site-specificity of the product, requiring the surgeon to predict where adhesions will occur and where they would most likely cause clinical problems. As an alternative to barriers, different fluids for intra-abdominal instillation such as icodextrin (Adept, Baxter Healthcare Corporation, IL, USA) or lactated Ringers' solution, have been administrated after the surgery in volumes sufficient to allow floatation of the abdominal structures and thus preventing the injured surfaces from reaching each other (Yaacobi et al. 1991. *Effect of Ringer's lactate irrigation on the formation of postoperative abdominal adhesions. J Invest Surg* 4, 31-36; Cavallari et al. 2000. *Inability of University of Wisconsin solution to reduce postoperative peritoneal adhesions in rats. Eur J Surg* 166, 650-653.; diZerega et al. supra). However, the gravity causes problems by preventing even distribution of the fluid in the abdomen. Also, the solutions are absorbed more rapidly from the abdominal cavity than the time required for peritoneal healing.

A limited number of pharmacologically active compounds have been tested in prevention of post-surgical adhesions. As some examples, the inflammatory component and fibroblast proliferation of the wound healing cascade has been a target of pharmacotherapy by using steroids drugs and cytotoxic drugs, respectively. However, these agents have shown ambiguous efficacy and potentially serious side effects (LeGrand et al. 1995. *Comparative efficacy of non-steroidal anti-inflammatory drugs and anti-thromboxane agents in a rabbit adhesion-prevention model. J Invest Surg* 8, 187-194; Li et al. 2004. *Synthesis and biological evaluation of a cross-linked hyaluronan-mitomycin C hydrogel. Biomacromolecules* 5, 895-902).

Due to the limited efficacy and difficult handling of the tested therapies, the vast majority of surgical interventions performed in abdominal cavity today, do not apply any products to prevent adhesion formation and the post-operational adhesions continue to cause suffering for the patients and present the major cost for society (Ray et al. 1998. *Abdominal adhesiolysis: inpatient care and expenditures in the United States in* 1994. *J Am Coll Surg* 186, 1-9.; 2005).

The object of the present invention is to provide a means which has the ability to prevent the formation of post-operative adhesion formation without having the unwanted side effects of the currently available pharmaceutical compositions, devices and procedures.

DESCRIPTION OF THE INVENTION

The present inventors describe the novel approach to prevent formation of intra-abdominal adhesions using biologically active peptides derived from human lactoferrin formulated in a pharmaceutical composition enhancing the therapeutic effect of the peptides. The biologically active peptides exhibit an inhibitory effect on the most important hallmarks of scar formation: reducing risk for infections, prohibiting inflammation and promoting fibrinolysis. The peptides are formulated together with the naturally occurring hydrophilic polymer hyaluronic acid, which provides slow release properties of the drug and contributes to the final results by physical barrier effect. Using a sidewall defect-cecum abrasion model in rats, generally accepted as adequate non-clinical predictor of clinical efficacy for anti-adhesive drugs, it is shown that biologically active peptides derived from human lactoferrin formulated in hyaluronic acid significantly reduce post-surgical intra-abdominal adhesions. The improved effect of the peptides when formulated in hyaluronic acid is unexpected, and significantly synergistic as compared to the effect of the peptides and the effect of hyaluronic acid given independently.

Accordingly, the present invention relates to pharmaceutical compositions enhancing the therapeutic effect of biologically active peptides, especially peptides derived from human lactoferrin.

One aspect the present invention provides a pharmaceutical composition for the treatment and/or prevention of wounds, scars, and post surgical adhesions comprising i) one or more biologically active peptides derived from human lactoferrin, and ii) a high molecular weight hyaluronic acid.

Another aspect of the present invention provides use of a i) one or more biologically active peptides derived from human lactoferrin, and ii) a high molecular weight hyaluronic acid for the manufacture of a pharmaceutical composition for the treatment and/or prevention of wounds, scars, and post surgical adhesions.

Yet another aspect of the present invention provides a method for the treatment, prophylaxis and/or prevention wounds, scars, and post surgical adhesions comprising the administration of a pharmaceutical composition comprising i) one or more biologically active peptides derived from human lactoferrin, and ii) a high molecular weight hyaluronic acid, to a subject in need of such treatment.

By "a biologically active peptide derived from human lactoferrin" is meant a biologically active peptide comprising at least one sequence motif which in part or in full is derived from the sequence of human lactoferrin, wherein this sequence motif can comprise one or more amino acid substitutions.

By "biologically active" peptides is meant peptides that have one or more activities, such as anti-inflammatory activity, immunomodulatory activity, fibrinolytic activity, anti-angiogenetic activity, and anti-microbial activity such as anti-bacterial activity, anti-viral activity, or anti-fungal activity.

Biologically active peptides suitable to be used according to the present invention are described in e.g. PCT/EP2008/064062, PCT/EP2008/065186, WO 00/01730, the corresponding EP 1095061 and U.S. Pat. No. 7,253,143, which hereby are incorporated by reference.

The biologically active peptide can be selected from peptides comprising the amino acid sequence

```
                                   (SEQ ID NO: 1)
Phe-X1-X2-X3-X4-X5-X6-X7-Lys-Val-Arg
```

wherein amino acid X1 is Gln or Ala, amino acid X2 is Trp or Leu, amino acid X3 is Gln, Ala, Orn, Nle or Lys, amino acid X4 is Arg, Ala or Lys, amino acid X5 is Asn, Ala, Orn or Nle, amino acid X6 is Met, Ala or Leu, amino acid X7 is Arg, Ala or Lys.

Preferably the biologically active peptide can be selected from peptides according to formula (I) and peptides according to formula (II)

```
                                          Formula (I)
R1-Cys-Phe-X1-X2-X3-X4-X5-X6-X7-Lys-Val-Arg-R2
```

wherein R1 is either no amino acid, Lys or a peptide sequence selected from Gly-Arg-Arg-Arg-Arg-Ser-Val-Gln-Trp-Cys-Ala-Val-Ser-Gln-Pro-Glu-Ala-Thr-Lys . . .

(SEQ ID NO:2) and N-terminally truncated fragments thereof including (SEQ ID NO: 57)
Arg-Arg-Arg-Arg-Ser-Val-Gln-Trp-Cys-Ala-Val-Ser-Gln-Pro-Glu-Ala-Thr-Lys, (SEQ ID NO: 58)
Arg-Arg-Arg-Ser-Val-Gln-Trp-Cys-Ala-Val-Ser-Gln-Pro-Glu-Ala-Thr-Lys, (SEQ ID NO: 59)
Arg-Arg-Ser-Val-Gln-Trp-Cys-Ala-Val-Ser-Gln-Pro-Glu-Ala-Thr-Lys, (SEQ ID NO: 60)
Arg-Ser-Val-Gln-Trp-Cys-Ala-Val-Ser-Gln-Pro-Glu-Ala-Thr-Lys, (SEQ ID NO: 61)
Ser-Val-Gln-Trp-Cys-Ala-Val-Ser-Gln-Pro-Glu-Ala-Thr-Lys, (SEQ ID NO: 62)
Val-Gln-Trp-Cys-Ala-Val-Ser-Gln-Pro-Glu-Ala-Thr-Lys, (SEQ ID NO: 63)
Gln-Trp-Cys-Ala-Val-Ser-Gln-Pro-Glu-Ala-Thr-Lys, (SEQ ID NO: 64)
Trp-Cys-Ala-Val-Ser-Gln-Pro-Glu-Ala-Thr-Lys, (SEQ ID NO: 65)
Cys-Ala-Val-Ser-Gln-Pro-Glu-Ala-Thr-Lys, (SEQ ID NO: 66)
Ala-Val-Ser-Gln-Pro-Glu-Ala-Thr-Lys, (SEQ ID NO: 67)
Val-Ser-Gln-Pro-Glu-Ala-Thr-Lys, (SEQ ID NO: 68)
Ser-Gln-Pro-Glu-Ala-Thr-Lys, (SEQ ID NO; 69)
Gln-Pro-Glu-Ala-Thr-Lys, (SEQ ID NO: 70)
Pro-Glu-Ala-Thr-Lys, (SEQ ID NO: 71)
Glu-Ala-Thr-Lys, Ala-Thr-Lys, Thr-Lys-;

and wherein R2 is either no amino acid, Gly or a peptide sequence selected from (SEQ ID NO: 3)
Gly-Pro-Pro-Val-Ser-Cys-Ile-Lys-Arg and C-terminally truncated fragments thereof including (SEQ ID NO: 72)
Gly-Pro-Pro-Val-Ser-Cys-Ile-Lys, (SEQ ID NO: 73)
Gly-Pro-Pro-Val-Ser-Cys-Ile, (SEQ ID NO: 74)
Gly-Pro-Pro-Val-Ser-Cys, (SEQ ID NO: 75)
Gly-Pro-Pro-Val-Ser, -continued (SEQ ID NO: 76)
Gly-Pro-Pro-Val, Gly-Pro-Pro,
and Gly-Pro Formula (II)

$$\text{R1-Phe-X1-X2-X3-X4-X5-X6-X7-Lys-Val-Arg-}\underset{\substack{|\alpha \\ \text{R3}}}{\text{X8}}\text{-R2}$$

wherein amino acid X8 is Gly, Lys, Glu or Asp;
when X8 is Gly then R3 is Ser-$(Arg)_n$-X9 and the bond α is a peptide bond between the carboxyl group of Gly and the amino group of Ser;
when X8 is Lys then R3 is X9-$(Arg)_n$-Ser and the bond a is an amide bond between the s-amino group in Lys and the carboxyl group in Ser; and
when X8 is Glu or Asp then R3 is Ser-$(Arg)_n$-X9 and the bond a an amide bond between the γ-carboxyl group of Glu or the β-carboxyl group of Asp and the amino group of Ser;
amino acid X9 is either no amino acid or Gly;
and n is an integer from 1 to 10, preferably an integer from 2 to 6, preferably an integer from 4 to 6, or even more preferably an integer from 3 to 4;
and wherein R1 is either no amino acid, Cys or a peptide sequence selected from (SEQ ID NO: 48)
y-Arg-Arg-Arg-Arg-Ser-Val-Gln-Trp-Cys-Ala-Val-Ser-Gln-Pro-Glu-Ala-Thr-Lys-Cys and N-terminally truncated fragments thereof including (SEQ ID NO: 77)
Gly-Arg-Arg-Arg-Arg-Ser-Val-Gln-Trp-Cys-Ala-Val-Ser-Gln-Pro-Glu-Ala-Thr-Lys-Cys, (SEQ ID NO: 78)
Arg-Arg-Arg-Arg-Ser-Val-Gln-Trp-Cys-Ala-Val-Ser-Gln-Pro-Glu-Ala-Thr-Lys-Cys, (SEQ ID NO: 79)
Arg-Arg-Arg-Ser-Val-Gln-Trp-Cys-Ala-Val-Ser-Gln-Pro-Glu-Ala-Thr-Lys-Cys, (SEQ ID NO: 80)
Arg-Arg-Ser-Val-Gln-Trp-Cys-Ala-Val-Ser-Gln-Pro-Glu-Ala-Thr-Lys-Cys, (SEQ ID NO: 81)
Arg-Ser-Val-Gln-Trp-Cys-Ala-Val-Ser-Gln-Pro-Glu-Ala-Thr-Lys-Cys, (SEQ ID NO: 82)
Ser-Val-Gln-Trp-Cys-Ala-Val-Ser-Gln-Pro-Glu-Ala-Thr-Lys-Cys, (SEQ ID NO: 83)
Val-Gln-Trp-Cys-Ala-Val-Ser-Gln-Pro-Glu-Ala-Thr-Lys-Cys, (SEQ ID NO: 84)
(Gln-Trp-Cys-Ala-Val-Ser-Gln-Pro-Glu-Ala-Thr-Lys-Cys, (SEQ ID NO: 85)
Trp-Cys-Ala-Val-Ser-Gln-Pro-Glu-Ala-Thr-Lys-Cys, -continued (SEQ ID NO: 86)
Cys-Ala-Val-Ser-Gln-Pro-Glu-Ala-Thr-Lys-Cys, (SEQ ID NO: 87)
Ala-Val-Ser-Gln-Pro-Glu-Ala-Thr-Lys-Cys, (SEQ ID NO: 88)
Val-Ser-Gln-Pro-Glu-Ala-Thr-Lys-Cys, (SEQ ID NO: 89)
Ser-Gln-Pro-Glu-Ala-Thr-Lys-Cys, (SEQ ID NO: 90)
Gln-Pro-Glu-Ala-Thr-Lys-Cys, (SEQ ID NO: 91)
Pro-Glu-Ala-Thr-Lys-Cys, (SEQ ID NO: 92)
Glu-Ala-Thr-Lys-Cys, (SEQ ID NO: 93)
Ala-Thr-Lys-Cys, Thr-Lys-Cys,
and Lys-Cys and wherein R2 is either no amino acid, Pro or a peptide sequence selected from (SEQ ID NO: 49)
Pro-Pro-Val-Ser-Cys-Ile-Lysand C-terminally truncated fragments thereof including (SEQ ID NO: 94)
Pro-Pro-Val-Ser-Cys-Ile-Lys, (SEQ ID NO: 95)
Pro-Pro-Val-Ser-Cys-Ile, (SEQ ID NO: 96)
Pro-Pro-Val-Ser-Cys, (SEQ ID NO: 97)
Pro-Pro-Val-Ser , Pro-Pro-Val,
and Pro-Pro;

Even more preferably the biologically active peptide can be selected from the peptides (SEQ ID NO: 4)
Ac-Glu-Ala-Thr-Lys-Cys-Phe-Gln-Trp-Gln-Arg-Asn-Met-Arg-Lys-Val-Arg-Gly-Pro-Pro-Val-Ser-Cys-Ile-Lys-Arg-$NH_2$ (SEQ ID NO: 5)
Thr-Lys-Cys-Phe-Gln-Trp-Gln-Arg-Asn-Met-Arg-Lys-Val-Arg-Gly-Pro-Pro-Val-Ser-Cys-Ile-Lys-Arg (SEQ ID NO: 6)
Val-Ser-Gln-Pro-Glu-Ala-Thr-Lys-Cys-Phe-Gln-Trp-Gln-Arg-Asn-Met-Arg-Lys-Val-Arg (SEQ ID NO: 7)
Glu-Ala-Thr-Lys-Cys-Phe-Gln-Trp-Gln-Arg-Asn-Met-Arg-Lys-Val-Arg (SEQ ID NO: 8)
Ser-Gln-Pro-Glu-Ala-Thr-Lys-Cys-Phe-Gln-Trp-Gln-Arg-Asn-Met-Arg-Lys-Val-Arg (SEQ ID NO: 9)
Gln-Pro-Glu-Ala-Thr-Lys-Cys-Phe-Gln-Trp-Gln-Arg-Asn-Met-Arg-Lys-Val-Arg (SEQ ID NO: 10)
Ala-Thr-Lys-Cys-Phe-Gln-Trp-Gln-Arg-Asn-Met-Arg-Lys-Val-Arg (SEQ ID NO: 11)
Thr-Lys-Cys-Phe-Gln-Trp-Gln-Arg-Asn-Met-Arg-Lys-Val-Arg (SEQ ID NO: 12)
Lys-Cys-Phe-Gln-Trp-Gln-Arg-Asn-Met-Arg-Lys-Val-Arg (SEQ ID NO: 13)
Cys-Phe-Gln-Trp-Gln-Arg-Asn-Met-Arg-Lys-Val-Arg (SEQ ID NO: 14)
Cys-Phe-Ala-Trp-Gln-Arg-Asn-Met-Arg-Lys-Val-Arg (SEQ ID NO: 15)
Cys-Phe-Gln-Trp-Ala-Arg-Asn-Met-Arg-Lys-Val-Arg (SEQ ID NO: 16)
Cys-Phe-Gln-Trp-Gln-Ala-Asn-Met-Arg-Lys-Val-Arg (SEQ ID NO: 17)
Cys-Phe-Gln-Trp-Gln-Arg-Ala-Met-Arg-Lys-Val-Arg (SEQ ID NO: 18)
Cys-Phe-Gln-Trp-Gln-Arg-Asn-Ala-Arg-Lys-Val-Arg (SEQ ID NO: 19)
Cys-Phe-Gln-Trp-Gln-Arg-Asn-Met-Ala-Lys-Val-Arg (SEQ ID NO: 20)
Cys-Phe-Gln-Leu-Gln-Arg-Asn-Met-Arg-Lys-Val-Arg (SEQ ID NO: 21)
Cys-Phe-Gln-Trp-Gln-Lys-Asn-Met-Arg-Lys-Val-Arg (SEQ ID NO: 22)
Cys-Phe-Gln-Trp-Gln-Arg-Asn-Leu-Arg-Lys-Val-Arg (SEQ ID NO: 23)
Cys-Phe-Gln-Trp-Gln-Arg-Asn-Met-Arg-Arg-Val-Arg (SEQ ID NO: 24)
Cys-Phe-Gln-Trp-Orn-Arg-Asn-Met-Arg-Lys-Val-Arg (SEQ ID NO: 25)
Cys-Phe-Gln-Trp-Nle-Arg-Asn-Met-Arg-Lys-Val-Arg (SEQ ID NO: 26)
Cys-Phe-Gln-Trp-Gln-Arg-Orn-Met-Arg-Lys-Val-Arg (SEQ ID NO: 27)
Cys-Phe-Gln-Trp-Gln-Arg-Nle-Met-Arg-Lys-Val-Arg (SEQ ID NO: 28)
Cys-Phe-Gln-Trp-Lys-Arg-Asn-Met-Arg-Lys-Val-Arg (SEQ ID NO: 29)
Cys-Phe-Gln-Trp-Lys-Arg-Ala-Met-Arg-Lys-Val-Arg (SEQ ID NO: 30)
Cys-Phe-Ala-Trp-Lys-Arg-Asn-Met-Arg-Lys-Val-Arg (SEQ ID NO: 31)
Cys-Phe-Ala-Trp-Gln-Arg-Ala-Met-Arg-Lys-Val-Arg (SEQ ID NO: 32)
Cys-Phe-Gln-Leu-Gln-Lys-Asn-Met-Lys-Lys-Val-Arg (SEQ ID NO: 33)
Cys-Phe-Ala-Leu-Lys-Lys-Ala-Met-Lys-Lys-Val-Arg (SEQ ID NO: 34)
Glu-Ala-Thr-Lys-Cys-Phe-Gln-Trp-Lys-Arg-Asn-Met-Arg-Lys-Val-Arg-Gly-Pro-Pro-Val-Ser-Cys-Ile-Lys-Arg -continued (SEQ ID NO: 35)
Ala-Thr-Lys-Cys-Phe-Gln-Trp-Lys-Arg-Asn-Met-Arg-Lys-Val-Arg-Gly-Pro-Pro-Val-Ser-Cys-Ile-Lys-Arg (SEQ ID NO: 36)
Thr-Lys-Cys-Phe-Gln-Trp-Lys-Arg-Asn-Met-Arg-Lys-Val-Arg-Gly-Pro-Pro-Val-Ser-Cys-Ile-Lys-Arg (SEQ ID NO: 37)
Lys-Cys-Phe-Gln-Trp-Lys-Arg-Asn-Met-Arg-Lys-Val-Arg-Gly-Pro-Pro-Val-Ser-Cys-Ile-Lys-Arg (SEQ ID NO: 38)
Glu-Ala-Thr-Lys-Cys-Phe-Gln-Trp-Lys-Arg-Asn-Met-Arg-Lys-Val-Arg-Gly-Pro-Pro-Val-Ser-Cys-Ile-Lys (SEQ ID NO: 39)
Glu-Ala-Thr-Lys-Cys-Phe-Gln-Trp-Lys-Arg-Asn-Met-Arg-Lys-Val-Arg-Gly-Pro-Pro-Val-Ser-Cys-Ile (SEQ ID NO: 40)
Glu-Ala-Thr-Lys-Cys-Phe-Gln-Trp-Lys-Arg-Asn-Met-Arg-Lys-Val-Arg-Gly-Pro-Pro-Val-Ser-Cys (SEQ ID NO: 41)
Glu-Ala-Thr-Lys-Cys-Phe-Gln-Trp-Lys-Arg-Ala-Met-Arg-Lys-Val-Arg-Gly-Pro-Pro-Val-Ser-Cys-Ile-Lys-Arg (SEQ ID NO: 42)
Ala-Thr-Lys-Cys-Phe-Gln-Trp-Lys-Arg-Ala-Met-Arg-Lys-Val-Arg-Gly-Pro-Pro-Val-Ser-Cys-Ile-Lys-Arg (SEQ ID NO: 43)
Thr-Lys-Cys-Phe-Gln-Trp-Lys-Arg-Ala-Met-Arg-Lys-Val-Arg-Gly-Pro-Pro-Val-Ser-Cys-Ile-Lys-Arg (SEQ ID NO: 44)
Lys-Cys-Phe-Gln-Trp-Lys-Arg-Ala-Met-Arg-Lys-Val-Arg-Gly-Pro-Pro-Val-Ser-Cys-Ile-Lys-Arg (SEQ ID NO: 45)
Glu-Ala-Thr-Lys-Cys-Phe-Gln-Trp-Lys-Arg-Ala-Met-Arg-Lys-Val-Arg-Gly-Pro-Pro-Val-Ser-Cys-Ile-Lys (SEQ ID NO: 46)
Glu-Ala-Thr-Lys-Cys-Phe-Gln-Trp-Lys-Arg-Ala-Met-Arg-Lys-Val-Arg-Gly-Pro-Pro-Val-Ser-Cys-Ile (SEQ ID NO: 47)
Glu-Ala-Thr-Lys-Cys-Phe-Gln-Trp-Lys-Arg-Ala-Met-Arg-Lys-Val-Arg-Gly-Pro-Pro-Val-Ser-Cys, and Ac-Phe-Gln-Trp-Gln-Arg-Asn-Met-Arg-Lys-Val-Arg-Lys-$NH_2$;
|
Gly-Arg-Arg-Arg-Ser Ac-Phe-Gln-Trp-Gln-Arg-Asn-Met-Arg-Lys-Val-Arg-Lys-$NH_2$;
|
Gly-Arg-Arg-Arg-Arg-Ser Ac-Phe-Gln-Trp-Gln-Arg-Ala-Met-Arg-Lys-Val-Arg-Lys-$NH_2$;
|
Gly-Arg-Arg-Arg-Arg-Ser Ac-Phe-Gln-Trp-Lys-Arg-Asn-Met-Arg-Lys-Val-Arg-Lys-$NH_2$;
|
Gly-Arg-Arg-Arg-Arg-Ser Ac-Phe-Gln-Trp-Lys-Arg-Ala-Met-Arg-Lys-Val-Arg-Lys-$NH_2$;
|
Gly-Arg-Arg-Arg-Arg-Ser Ac-Phe-Gln-Trp-Gln-Arg-Asn-Met-Arg-Lys-Val-Arg-Lys-$NH_2$
|
Ac-Gly-Arg-Arg-Arg-Arg-Arg-Ser Ac-Phe-Gln-Trp-Gln-Arg-Asn-Met-Arg-Lys-Val-Arg-Lys-$NH_2$
|
Ac-Gly-Arg-Arg-Arg-Arg-Arg-Arg-Ser Ac-Phe-Gln-Trp-Gln-Arg-Asn-Met-Arg-Lys-Val-Arg-Glu-$NH_2$
|
Ser-Arg-Arg-Arg-Arg-Gly-$NH_2$;

Ac-Phe-Gln-Trp-Gln-Arg-Ala-Met-Arg-Lys-Val-Arg-Glu-$NH_2$
|
Ser-Arg-Arg-Arg-Arg-Gly-$NH_2$;

Ac-Phe-Gln-Trp-Lys-Arg-Asn-Met-Arg-Lys-Val-Arg-Glu-$NH_2$
|
Ser-Arg-Arg-Arg-Arg-Gly-$NH_2$;

Ac-Phe-Gln-Trp-Lys-Arg-Ala-Met-Arg-Lys-Val-Arg-Glu-$NH_2$
|
Ser-Arg-Arg-Arg-Arg-Gly-$NH_2$;

Ala-Thr-Lys-CysM-Phe-Gln-Trp-Gln-Arg-Ala-Met-Arg-Lys-Val-Arg-Lys-Pro-Pro-Val-Ser-CysM-Ile-Lys-Arg;
|
Gly-Arg-Arg-Arg-Arg-Ser

Ac-Phe-Gln-Trp-Gln-Arg-Ala-Met-Arg-Lys-Val-Arg-Lys-Pro-Pro-Val-Ser-CysM-Ile-Lys-Arg;
|
Gly-Arg-Arg-Arg-Arg-Ser

Ala-Thr-Lys-CysM-Phe-Gln-Trp-Gln-Arg-Ala-Met-Arg-Lys-Val-Arg-Lys-$NH_2$;
|
Gly-Arg-Arg-Arg-Arg-Ser

Ala-Thr-Lys-CysM-Phe-Gln-Trp-Lys-Arg-Ala-Met-Arg-Lys-Val-Arg-Lys-Pro-Pro-Val-Ser-CysM-Ile-Lys-Arg;
|
Gly-Arg-Arg-Arg-Arg-Ser

Ac-Phe-Gln-Trp-Lys-Arg-Ala-Met-Arg-Lys-Val-Arg-Lys-Pro-Pro-Val-Ser-CysM-Ile-Lys-Arg;
|
Gly-Arg-Arg-Arg-Arg-Ser

Ac-Phe-Gln-Trp-Gln-Arg-Asn-Met-Arg-Lys-Val-Arg-Lys-Pro-Pro-Val-Ser-CysM-Ile-Lys-Arg-$NH_2$
|
Ac-Gly-Arg-Arg-Arg-Arg-Arg-Arg-Ser

Ala-Thr-Lys-CysM-Phe-Gln-Trp-Lys-Arg-Ala-Met-Arg-Lys-Val-Arg-Lys-$NH_2$;
|
Gly-Arg-Arg-Arg-Arg-Ser

Ala-Thr-Lys-CysM-Phe-Gln-Trp-Gln-Arg-Ala-Met-Arg-Lys-Val-Arg-Glu-Pro-Pro-Val-Ser-CysM-Ile-Lys-Arg;
|
Ser-Arg-Arg-Arg-Arg-Gly-$NH_2$

-continued

Ac-Phe-Gln-Trp-Gln-Arg-Ala-Met-Arg-Lys-Val-Arg-Glu-Pro-Pro-Val-Ser-CysM-Ile-Lys-Arg;
|
Ser-Arg-Arg-Arg-Arg-Gly-$NH_2$

Ala-Thr-Lys-CysM-Phe-Gln-Trp-Gln-Arg-Ala-Met-Arg-Lys-Val-Arg-Glu-$NH_2$
|
Ser-Arg-Arg-Arg-Arg-Gly-$NH_2$;

Ala-Thr-Lys-CysM-Phe-Gln-Trp-Lys-Arg-Ala-Met-Arg-Lys-Val-Arg-Glu-Pro-Pro-Val-Ser-CysM-Ile-Lys-Arg;
|
Ser-Arg-Arg-Arg-Arg-Gly-$NH_2$

Ac-Phe-Gln-Trp-Lys-Arg-Ala-Met-Arg-Lys-Val-Arg-Glu-Pro-Pro-Val-Ser-CysM-Ile-Lys-Arg;
|
Ser-Arg-Arg-Arg-Arg-Gly-$NH_2$

Ac-Phe-Gln-Trp-Lys-Arg-Ala-Met-Arg-Lys-Val-Arg-Glu-$NH_2$
|
Ser-Arg-Arg-Arg-Arg-Arg-Arg-Gly-$NH_2$

Ala-Thr-Lys-CysM-Phe-Gln-Trp-Lys-Arg-Ala-Met-Arg-Lys-Val-Arg-Glu-$NH_2$
|
Ser-Arg-Arg-Arg-Arg-Gly-$NH_2$;

(SEQ ID NO: 50)
Ac-Phe-Gln-Trp-Gln-Arg-Asn-Met-Arg-Lys-Val-Arg-Gly-Ser-Arg-Arg-Arg-Arg-Gly-$NH_2$;

(SEQ ID NO: 51)
Ala-Thr-Lys-CysM-Phe-Gln-Trp-Gln-Arg-Asn-Met-Arg-Lys-Val-Arg-Gly-Ser-Arg-Arg-Arg-Arg-Gly-$NH_2$;

(SEQ ID NO: 52)
Ac-Phe-Gln-Trp-Lys-Arg-Asn-Met-Arg-Lys-Val-Arg-Gly-Ser-Arg-Arg-Arg-Arg-Gly-$NH_2$;

(SEQ ID NO: 53)
Ala-Thr-Lys-CysM-Phe-Gln-Trp-Lys-Arg-Asn-Met-Arg-Lys-Val-Arg-Gly-Ser-Arg-Arg-Arg-Arg-Gly-$NH_2$;

(SEQ ID NO: 54)
Ac-Phe-Gln-Trp-Lys-Arg-Ala-Met-Arg-Lys-Val-Arg-Gly-Ser-Arg-Arg-Arg-Arg-Gly-$NH_2$;

(SEQ ID NO: 55)
Ala-Thr-Lys-CysM-Phe-Gln-Trp-Lys-Arg-Ala-Met-Arg-Lys-Val-Arg-Gly-Ser-Arg-Arg-Arg-Arg-Gly-$NH_2$;

Most preferably the biologically active peptide is selected from the peptides

```
                                    (SEQ ID NO: 4)
Ac-Glu-Ala-Thr-Lys-Cys-Phe-Gln-Trp-Gln-Arg-Asn-
Met-Arg-Lys-Val-Arg-Gly-Pro-Pro-Val-Ser-Cys-Ile-
Lys-Arg-NH2
and
                                   (SEQ ID NO: 50)
Ac-Phe-Gln-Trp-Gln-Arg-Asn-Met-Arg-Lys-Val-Arg-
Gly-Ser-Arg-Arg-Arg-Arg-Gly-NH2;
```

Peptides comprising two cysteine residues can be in the form of a cyclic peptide structure where the two cysteines form a cysteine bridge.

Accordingly, one preferred biologically active peptide is the peptide (SEQ ID NO: 56)

Ac-Glu-Ala-Thr-Lys-Cys-Phe-Gln-Trp-Gln-Arg-Asn-Met-Arg
| |
$H_2N$-Arg-Lys-Ile-Cys-Ser-Val-Pro-Pro-Gly-Arg-Val-Lys

When present, it may be advantageous to replace the amino acid Cys by an acetamidomethyl-cysteine (indicated as CysM) in order to avoid that the peptide forms a disulphide bridge with another peptide comprising a cysteine.

According to one preferred aspect of the invention the carboxy terminal end of the peptide has been capped, i.e. the free COOH at the carboxy terminal end has been transformed, e.g. by amidation into $CONH_2$. (indicated as —$NH_2$)

According to another preferred aspect of the invention the amino terminal end of the peptide has been capped, i.e. the free $NH_2$ group at the amino terminal has been transformed, e.g. by acetylation into the amide $CH_3CONH$— (indicated as Ac—).

According to yet another preferred aspect of the invention both the carboxy-terminal and the amino-terminal ends of the peptide have been capped.

In the case where a peptide according to the invention is described as being capped at the carboxy terminal end and/or amino terminal end, it is also possible according to the invention to use the corresponding uncapped peptide.

In the case where a peptide according to the invention is described as being uncapped at the carboxy terminal end and/or amino terminal end, it is also possible according to the invention to use the corresponding capped peptide.

The advantage of the capped versions is that N- and C-terminal amino acids of these peptides are neutral and uncharged and thus has changed electrostatic properties. Assuming that the receptors bind the corresponding sequences of human lactoferrin where there are no N- and C terminal charges, the capped peptides should bind better as they in this respect resemble the native protein more than uncapped peptides.

Preferably the biologically active peptide is present in the pharmaceutical composition at a concentration between 0.1 mg/ml and 100 mg/ml, most preferably between 0.5 mg/ml and 25 mg/ml.

The biologically active peptide can be present in the form of a pharmaceutical acceptable salt.

Preferably the high molecular weight hyaluronic acid has a molecular weight higher than 300,000 Da, most preferably higher than 800,000 Da.

Preferably the high molecular weight hyaluronic acid is present in the pharmaceutical composition at a concentration between 0.1 and 10% (w/w), most preferably between 0.5 and 2.5% (w/w).

The high molecular weight hyaluronic acid can be present in the form of a pharmaceutical acceptable salt.

The pharmaceutical compositions according to the invention can be used to prevent the formation of post surgical scars, adhesions, keloids in connection with surgical procedures on various tissues such as skin, muscles, tendons, nervous tissue, blood vessels, and at different locations of the body such as eyes, ears, vocal cord, hand, spinal cord, intra-abdominal cavity, intra-thoracic cavity, intra-cranial cavity, oral cavity, gynaecological procedures, endometrios, phimosis.

The present inventors have unexpectedly found that the biological effect of the peptides derived from human lactoferrin can be significantly enhanced if the peptides are administered in a pharmaceutical composition comprising the peptide together with a high molecular weight hyaluronic acid.

This enhancement can not be explained only by a possible effect of the hyaluronic acid as such, but is due to an unexpected synergistic effect.

The behaviours of PXL01 loaded sodium hyaluronate gels at 37° C. The concentration of PXL01 is 6 mg/ml in 1.5% sodium hyaluronate solution. The cumulative drug released was expressed as the % drug released at time t. The data are shown as mean±SDV of three independent product preparations with the moving average trendline added.

Figure 2:
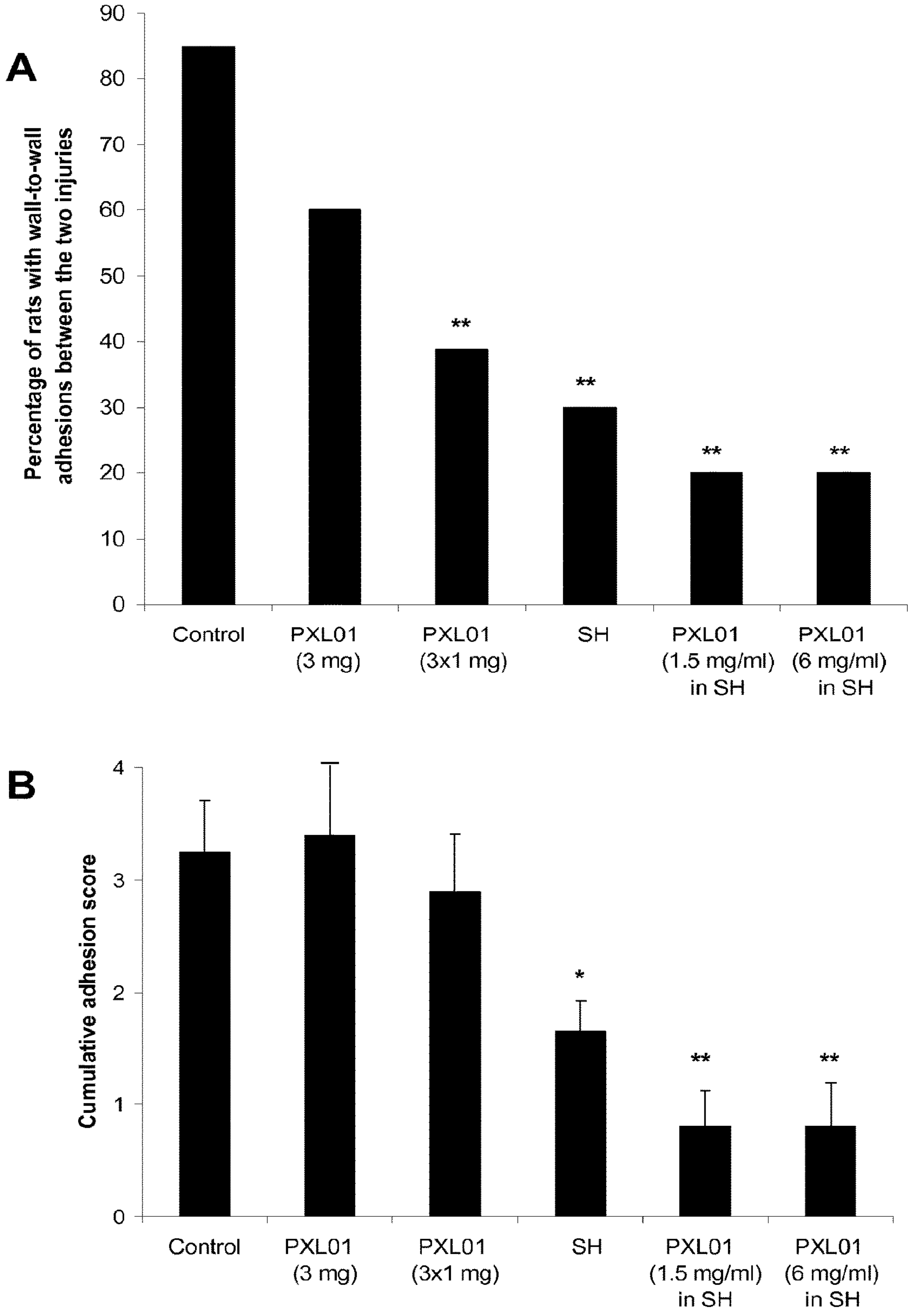
Figure 2:
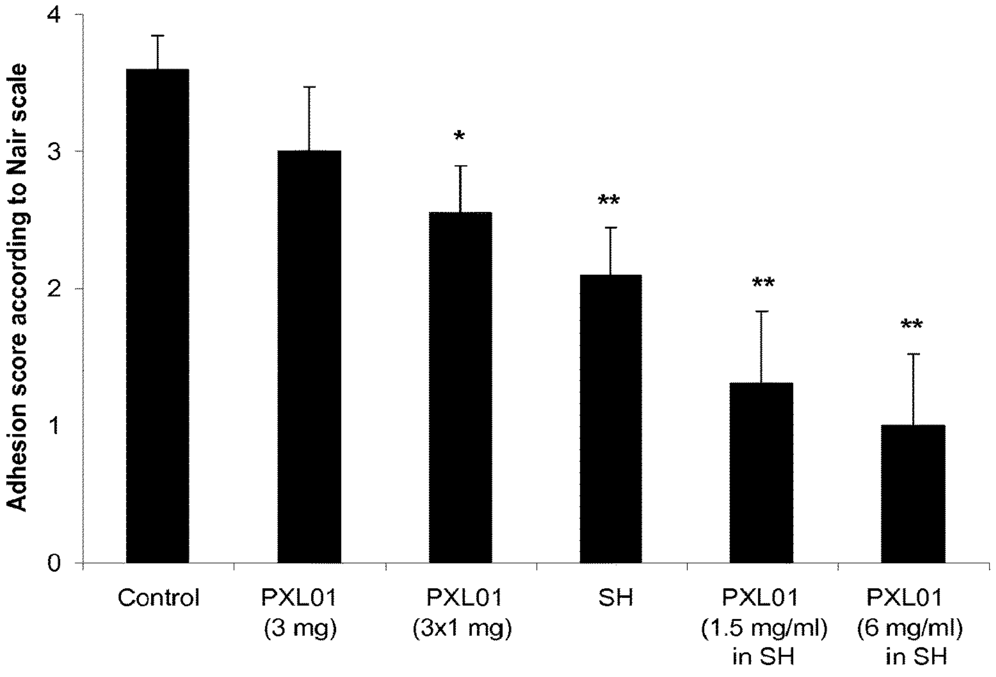
Figure 2:
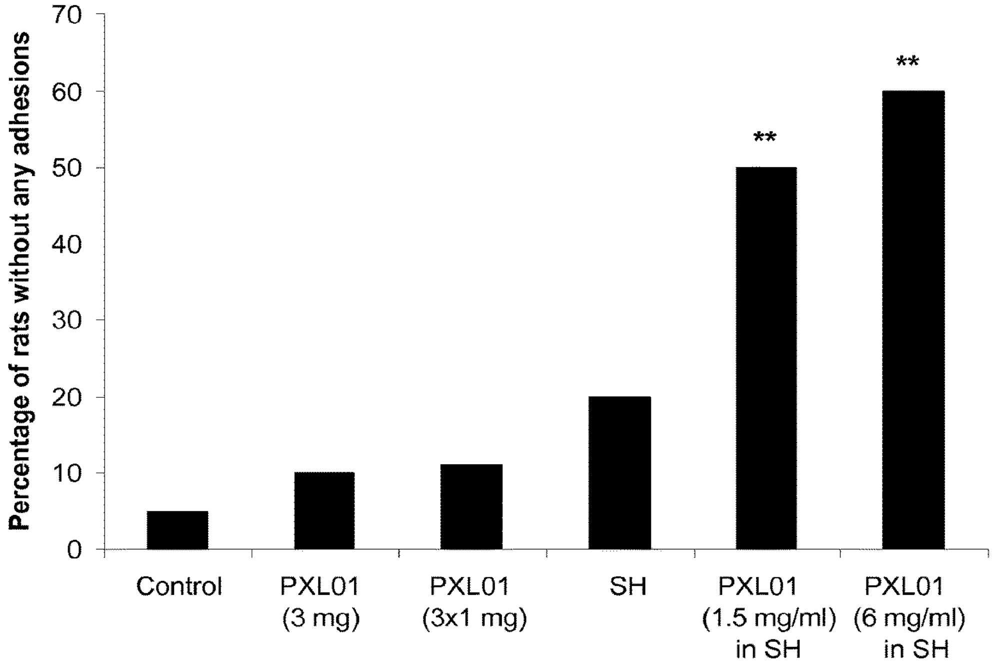
Figure 2:
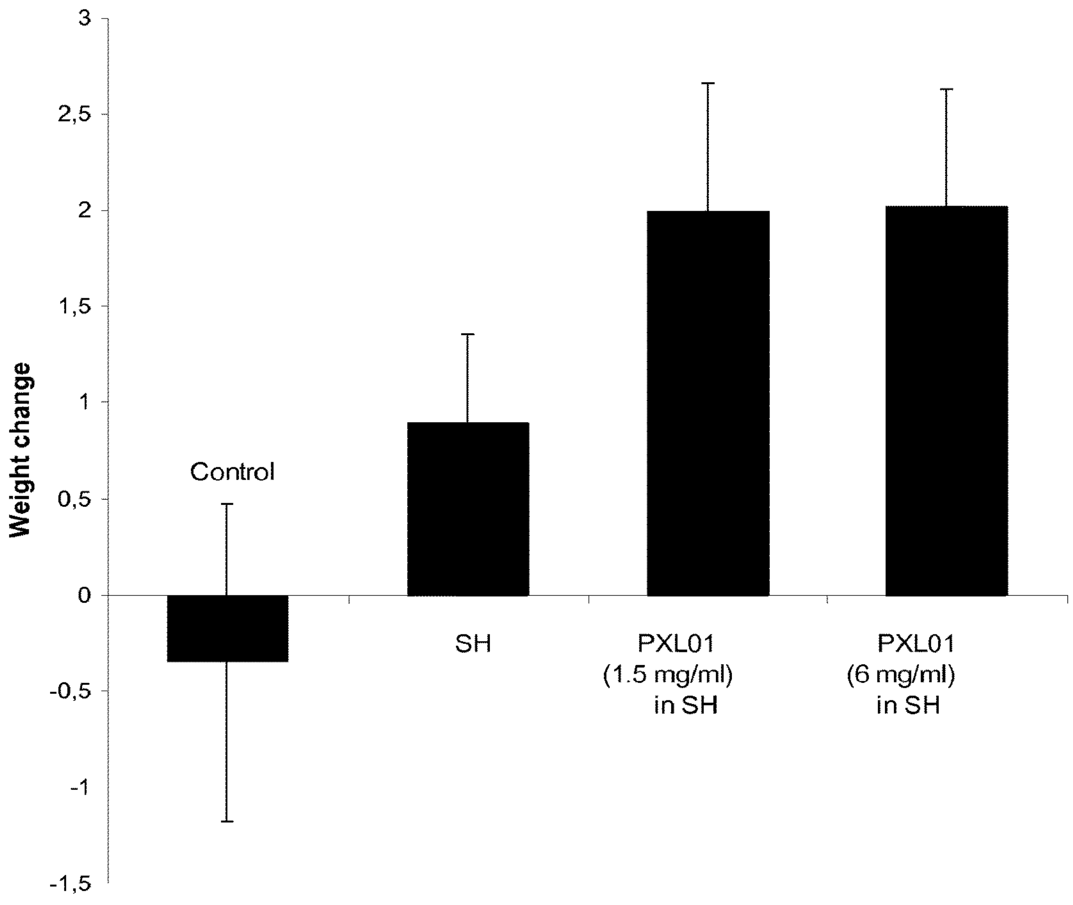

FIG. 2. PXL01 prevents adhesion formation in rat model of abdominal surgery.

(A) The incidence of adhesion formation between the injury sites of abdominal wall and cecum, presented as a percentage of animals developing wall to wall adhesion connecting these injuries in each group. (B) The cumulative scoring scale showing the total number of adhesions found in the abdominal cavity presented as mean±SEM. (C) The adhesion scores according to the Nair scale presented as mean±SEM (scoring criteria listed in Examples). (D) Percentage of animals without any adhesion formation in the abdominal cavity in each group. (E) Weight change during the 6 survival days after surgery presented as percentage of initial weight. n(control)=20, n(1 administration of 0.5 ml PXL01 (6 mg/ml) in dH2O)=10, n(3 administrations of 0.5 ml PXL01 (2 mg/ml) in dH2O in connection to the operation and 24 and 48 h post-surgery)=18, n(1 administration of 1.5% sodium hyaluronate)=20, n(1 administration of 1 ml PXL01 (1.5 mg/ml) in 1.5% sodium hyaluronate)=10, n(1 administration of 1.5 ml PXL01 (6 mg/ml) in 1.5% sodium hyaluronate)=10). Statistical significance was estimated by Fisher's exact test (A, D) or by non-parametric Mann Whitney test (B, C). *, $p<0.05$; **, $p<0.01$ indicate statistical difference compared to the surgical control group of animals. Adm, administration; SH, sodium hyaluronate, dH20, distilled water.

EXAMPLES

Experimental

Peptide

The peptide PXL01 (SEQ ID NO:56) was used in the experiments.

Preparation of PXL01 in Sodium Hyaluronate Hydrogels

PXL01 dissolved in sodium chloride solution was added to 2.5% sodium hyaluronate solution at a volume ratio of 2/5 PXL01 solution and 3/5 sodium hyaluronate solution, to obtain 1.5 or 6 mg/ml PXL01 in 1.5% sodium hyaluronate. The solutions were homogenized by drawing the mixtures several times through 2.1 mm diameter needles.

Characterization of Formulated Product

PXL01 concentration and homogeneity in sodium hyaluronate were determined by high performance liquid chromatography with UV detector (Agilent model 1100) at 220 nm. The analytical column used was a Vydac 218TP (C18, 5 μm, 250×4.6 mm). The mobile phases used (0.1% TFA in water containing 1% acetonitrile (solvent A) and 0.1% TFA in acetonitrile (solvent B)) were run at a gradient with a flow rate of 1.0 ml/min. Diluted PXL01 standards were applied to create calibration curves.

Samples were prepared by adding hyaluronidase solution (Hyaluronidase from *Streptomyces hyalurolyticus*, Sigma-Aldrich, St Louis, Mo.) with an enzyme activity of 500 units/ml to sample solutions. The mixtures were agitated for 2 h at room temperature and samples were diluted as needed with TFA in water, followed by additional mixing. The samples were centrifuged at 7000 rpm for 5 min before injection to the column.

In Vitro Release System Setup 0.25 ml of the formulated product was placed into the well of the tissue culture plate (24-Flat Well Tissue Culture Plate, Techno Plastic Products AG), resulting in a thin film of approximately 1.3 mm. The plates were placed into thermostat (37° C.) for 1 h to allow the product to reach the temperature of 37° C. 0.5 ml of the release medium (PBS, pH 7.4) re-equilibrated at 37° C. was carefully layered over the surface of the gel and the tissue culture plates were transferred into a thermostatic shaker (60 rpm, 37° C.). At predetermined time intervals, 10 microl aliquots of the aqueous solution were withdrawn from the release media. The concentration of PXL01 released was monitored at wavelength of 230 nm using a spectrophotometric measurement. Because the measurement of absorbance at 230 nm could detect the peptide as well as dissolved sodium hyaluronate in the release medium, a control release medium was used which has the same amount of sodium hyaluronate without any PXL01 as that of sodium hyaluronate with the drug.

Animal Models for Assessment of Post-Surgical Adhesion Prevention

Female Sprague-Dawley rats (200-250 g, Charles River Laboratories, Sulzfeldt, Germany) were kept in a 12 hours light-dark cycle and were cared for in accordance with regulations for the protection of laboratory animals. The study was performed after prior approval from the local ethical committee.

Cecum abrasion and excision of the abdominal wall were performed to induce de novo adhesions as described previously (Harris et al. 1995. *Analysis of the kinetics of peritoneal adhesion formation in the rat and evaluation of potential antiadhesive agents. Surgery* 117, 663-669). Briefly, the rats were anaesthetized with isoflurane (Isoba®vet, Shering-Plough Animal Health, Farum, Denmark) and buprenorfin (48 microg/kg, Temgesic, Shering-Plough, Brussels, Belgium) was given as post-operative pain reliever. A 5-cm-long midline incision of the abdomen was performed and a rectangle full thickness injury (5 mm×25 mm) was made on the peritoneal wall through both the parietal peritoneum and the muscular fascia. Also, an area of the serous membrane on the both sides of the cecum, approximately 10 mm×15 mm, was gently rubbed using cotton gauze until petechial hemorrhages appeared. The rats were randomized to untreated control group or treated groups. Excessive blood from the injury was removed and the test substance was applied over the abraded areas using a syringe. The laparotomy wound was closed with a continuous suture and the skin was closed with metal clips (Appose ULC35W, TycoHealthcare Group LP, Norwalk, Conn., US). The animals were killed 6 days after surgery with an overdose of pentobarbital sodium (Pentobarbital vet, APL, Stockholm, Sweden). The abdomen was opened and the adhesions were scored by an evaluator blinded to the treatment. The incidence of adhesions between abdominal incision and the abraded cecum was quantified as a percentage of animals developing wall to wall adhesions connecting these injuries, in each group. Additionally, to comprehensively evaluate the total number of adhesions formed in the abdominal cavity, including the adhesions remote from the surgical trauma, two different grading schemes were used. The cumulative scoring scale described by Bothin (Bothin et al. 2001. *The intestinal flora influences adhesion formation around surgical anastomoses. Br J Surg* 88, 143-145) assigns the total number of adhesions present in the abdominal cavity: one point is given to each adhesion observed and the points are added to form the score. The adhesion scoring scale according to Nair (Nair et al. 1974. *Role of proteolytic enzyme in the prevention of postoperative intraperitoneal adhesions. Arch Surg* 108, 849-85) incorporates both the total number of adhesions and the incidence of adhesions between target organs, while a higher grading is given to the latter one (0, no adhesions; 1, single band of adhesions from the viscera to the target organ; 2, two bands of adhesions from the viscera to the target organ; 3, more than two adhesive bands from the viscera to the target organ, 4, viscera directly adherent to abdominal wall, irrespective of number and extent of adhesive bands). Finally, the percentage of rats free from any abdominal adhesions was assessed in each group. Any possible signs of peritoneal inflammation (erythema and/or edema) or disrupted wound healing were recorded in connection to the necropsies. As a general marker for well being, the body weights of animals before and 6 days after the surgery were compared.

Large Bowel Anastomosis Model in the Rat

Female Sprague Dawley rats (200-250 g, Charles River Laboratories, Sulzfeldt, Germany) were kept at a 12 hours light-dark cycle and were cared for in accordance with regulations for the protection of laboratory animals. The study was conducted after prior approval from the local ethical committee. Anaesthesia was induced with isoflurane (Isoba®vet, Shering-Plough Animal Health, Farum, Denmark) and the rats received buprenorfin (48 microg/kg; Temgesic, Shering-Plough, Brussels) intramuscularly for post-operative pain relieve and Bimotrim (80 mg/kg; Bimeda, UK,) subcutaneously before the surgery.

The abdominal wall was shaved and a midline laparatomy of approximately 3 cm was performed. The colon was exposed and transected 2 cm distal of cecum. A seromuscular end-to-end anastomosis was performed with 8 interrupted sutures using 6/0 monocryl (Y432H, Ethicon Inc, St-Stevens Woluwe, Belgium) thread. A macaroon was placed in colon at anastomosis as stent during suturing. The rats were randomly divided into groups receiving PXL01 (6 mg/ml) in 1.5% sodium hyaluronate covering the anastomosis and surrounding peritoneum (n=8) or no treatment (n=8). The abdomen was closed with a continuous suture (4-0 monocryl, Y3100H, Ethicon Inc.) in the muscular layer and with staplers in the skin. 2 ml isotonic saline was administered subcutaneously to prevent dehydration.

The animals received additional doses of buprenorfin (24 microg/kg; Temgesic, Shering-Plough, Brussels) subcutaneously two times per day for two days after surgery. The animals were killed 7 days after surgery with an overdose of pentobarbital sodium (Pentobarbital vet, APL, Stockholm, Sweden). The abdomen was opened and a 4-cm-long intestinal segment was resected with the anastomosis area located in the middle. A tube connected to a pressure monitor was inserted into one side of the intestinal segment and the other side was ligated at the end. The intestinal segment was placed immediately under isotonic sodium chloride, stained saline was infused through the tube into the intestinal segment, and the intraluminar pressure was monitored using a Grass recorder (Grass Instruments Co, Quincy, Ohio, USA). The maximum pressure prior to anastomotic burst was recorded as the burst pressure. The appearance of stained saline around the anastomosis indicated the time point for the burst. The evaluator was blinded to the treatment each animal received.

Results

PXL01 Release Behaviour in Sodium Hyaluronate

Figure 1:
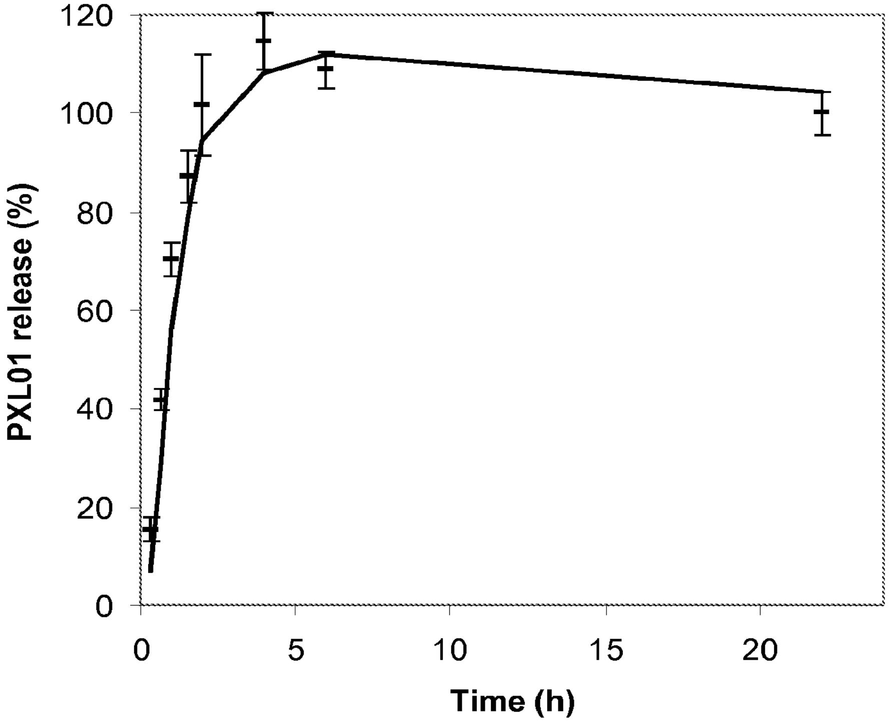
FIG. 1. The behaviours of PXL01 loaded sodium hyaluronate gels at 37° C.

PXL01 dissolved in sodium chloride solution was mixed with the sodium hyaluronate solution resulting in homogenous PXL01-containing hydrogel. The in vitro release experiments revealed a burst release of PXL01 from the sodium hyaluronate gel formulation with approximately 70% of PXL01 released within 1 hour (FIG. 1). Release behaviour characterized by an initial burst is already demonstrated for other soluble compounds formulated in sodium hyaluronate (Sherwood et al. 1992. *Controlled antibody delivery systems. Biotechnology* (N Y) 10, 1446-1449). This may have a functional use in providing an initial dose during drug delivery, minimizing any lag period. Importantly, the release profiles of PXL01 from the formulated products prepared in three independent occasions were largely overlapping indicating that preparation of PXL01-loaded sodium hyaluronate gels is highly reproducible (FIG. 1).

Prevention of Peritoneal Adhesions by PXL01

The sidewall defect-cecum abrasion model in rat (Arnold et al. supra) was used to elucidate the anti-adhesion effect of PXL01. This model produces reliable and consistent adhesions between the two injured surfaces if no treatment is given, with 85% of the rats in the control group developing direct cecum-peritoneal wall adhesions (FIG. 2A). No significant reduction in adhesion formation was observed when 3 mg of PXL01 in water solution was administrated as a single dose in connection to the surgery (FIGS. 2A-D). However, animals treated with 3 doses of 1 mg of PXL01 in water solution demonstrated marked reduction in adhesion formation compared with the control group of rats (FIGS. 2A, C). These results indicate that slow release of PXL01 in the surgical area is beneficial, compared to the single treatment with the water solution of the peptide.

Sodium hyaluronate was chosen as carrier to achieve controlled release of PXL01. PXL01 appears readily soluble and sufficiently stable in sodium hyaluronate, also the PXL01-containing sodium hyaluronate hydrogel is bioadhesive and easy to apply to the surgical area using a syringe. When PXL01 was applied in 1.5% high molecular weight sodium hyaluronate formulation, the formation of abdominal adhesions was significantly reduced, compared with the control group. There was a 4-fold reduction according to the cumulative adhesion scoring scale (FIG. 2B) and more than 3-fold reduction of the adhesion score according to Nair (FIG. 2C). 60% of animals treated with 6 mg/ml PXL01 in sodium hyaluronate were completely free from adhesions compared with 5% of the animals in control group and 20% of animals in the group treated with sodium hyaluronate (FIG. 2D). By several scoring scales, sodium hyaluronate per se was shown to reduce adhesion formation, presumably due to the physical barrier effect (Burns et al. 1995. *Prevention of tissue injury and postsurgical adhesions by precoating tissues with hyaluronic acid solutions. J Surg Res* 59, 644-652).

No treatment-related adverse effects were recorded during the study regarding the wound healing or peritoneal inflammation assessed during necropsies. Also, the average body weight of the rats in the treatment groups was increased compared to their pre-surgical weights, although the difference compared to the control group did not reach statistical significance (FIG. 2E). Importantly, PXL01 in sodium hyaluronate administered around the intestinal anastomosis did not reduce the healing potential as estimated by the burst pressure of anastomosis measured 7 days after the surgery (burst pressure for the treatment group (n=8) 206.3±14.3 mm Hg versus 197.4±9.6 mm Hg in the sham group (n=8)).

The ability of PXL01 to prevent adhesions was limited in water solution (FIGS. 2A-D), possibly due to the fact that the peptide is rapidly eliminated from the peritoneum. However, the peptide was highly effective formulated in sodium hyaluronate (FIGS. 2A-D), causing significant reduction of adhesions according to different grading scales encompassing both the adhesions formed between the two injured surfaces as well as in the abdominal areas remote form the site of application. Sodium hyaluronate, a natural component of extracellular matrix, is catabolized locally or carried to lymph notes or the general circulation, from where it is cleared by the endothelial cells of the liver (Fraser et al. 1988. *Uptake and degradation of hyaluronan in lymphatic tissue. Biochem J* 256, 153-158; Laurent & Fraser 1992. *Hyaluronan. Faseb J* 6, 2397-2404). Sodium hyaluronate is likely to enhance the effect of PXL01 by maintaining local concentrations of the drug through controlled release. In vitro experiments indicate a relatively brief period of PXL01 release from sodium hyaluronate (FIG. 1) suggesting that the duration of the drug release required for adhesion prevention in vivo may be rather limited. This is in line with the previous evidence that the critical events in adhesion formation in abdominal cavity occur in the first 36 h (Harris et al. 1995. *Analysis of the kinetics of peritoneal adhesion formation in the rat and evaluation of potential antiadhesive agents. Surgery* 117, 663-669). Previously, several carrier systems based on microparticles have been shown to induce adhesions or cause inflammation (Hockel et al. 1987. *Prevention of peritoneal adhesions in the rat with sustained intraperitoneal dexamethasone delivered by a novel therapeutic system. Ann Chir Gynaecol* 76, 306-313; Kohane et al. 2006. *Biodegradable polymeric microspheres and nanospheres for drug delivery in the peritoneum. J Biomed Mater Res A* 77, 351-361). No obvious adverse events such as listlessness, peritoneal inflammation or inhibition of wound healing were observed in animals treated with PXL01 at any concentration. At the time of sacrifice all treatment groups had maintained or exceeded their pre-surgery weights (FIG. 2E). Importantly, PXL01 in sodium hyaluronate administered around the intestinal anastomosis did not interfere with the healing potential of the anastomosis.

In summary, the present inventors describe an unexpected observation that the biological effect of the lactoferrin-derived peptides on prevention of post-surgical adhesion formation can be significantly enhanced if the peptides are administered in a pharmaceutical composition comprising the peptide together with a high molecular weight hyaluronic acid. The effect is significantly synergistic as compared to the effect of the peptide and the effect of hyaluronic acid given independently. Previously, several carrier systems based on microparticles have been shown to induce adhesions or cause inflammation (Hockel et al. 1987. supra; Kohane et al. 2006. supra). Also, applications of physical barriers for adhesion prevention have been shown to lead to adverse effects such as anastomosis leak, due to interference with the wound healing process (diZerega et al. 2002. supra). In the present study, sodium hyaluronate was shown not to increase adhesions but rather to act synergistically to lactoferrin peptides in adhesion prevention. Importantly, administration of the peptides in sodium hyaluronate was not associated with any safety concern regarding healing of anastomosis and thus, the product demonstrated the superior safety profile compared to the previously described anti-adhesive agents. The peptide-loaded sodium hyaluronate gel is easy to handle and administrate and is compatible with laparatomy or laparoscopy. Taken together, the product is expected to give comprehensive adhesion prevention regime preventing not only the adhesions which form at sites of operative procedures, but also de novo adhesions that form to sites not directly involved in surgery due to unintentional tissue injury during surgical manipulation, without causing any adverse effects on healing.

The invention claimed is:

1. A pharmaceutical composition comprising in admixture:

(i) the peptide PXL01 (SEQ ID NO:56), or a pharmaceutically acceptable salt thereof; and (ii) a high molecular weight hyaluronic acid having an average molecular weight higher than 300 000 Da, or a pharmaceutically acceptable salt thereof.

2. The pharmaceutical composition according to claim 1, wherein the high molecular weight hyaluronic acid has an average molecular weight higher than 800 000 Da.

3. The pharmaceutical composition according to claim 1, wherein the peptide PXL01 (SEQ ID NO:56) is present at a concentration of between 0.1 mg/ml and 100 mg/ml.

4. The pharmaceutical composition according to claim 2, wherein the peptide PXL01 (SEQ ID NO:56) is present at a concentration of between 0.1 mg/ml and 100 mg/ml.

5. The pharmaceutical composition according to claim 3, wherein the peptide PXL01 (SEQ ID NO:56) is present at a concentration of between 0.5 mg/ml and 25 mg/ml.

6. The pharmaceutical composition according to claim 4, wherein the peptide PXL01 (SEQ ID NO:56) is present at a concentration of between 0.5 mg/ml and 25 mg/ml.

7. The pharmaceutical composition according to any one of claims 1-6, wherein the high molecular weight hyaluronic acid is present at a concentration of between 0.1 and 10% (w/w).

8. The pharmaceutical composition according to claim 7, wherein the high molecular weight hyaluronic acid is present at a concentration of between 0.5 and 2.5% (w/w).

* * * * *

SEQUENCE LISTING

```
<160> NUMBER OF SEQ ID NOS: 97

<210> SEQ ID NO 1
<211> LENGTH: 11
<212> TYPE: PRT
<213> ORGANISM: Artificial
<220> FEATURE:
<223> OTHER INFORMATION: Sequence derived from human lactoferrin
<220> FEATURE:
<221> NAME/KEY: VARIANT
<222> LOCATION: (2)..(2)
<223> OTHER INFORMATION: Xaa = Gln or Ala
<220> FEATURE:
<221> NAME/KEY: VARIANT
<222> LOCATION: (3)..(3)
<223> OTHER INFORMATION: Xaa = Trp or Leu
<220> FEATURE:
<221> NAME/KEY: VARIANT
<222> LOCATION: (4)..(4)
<223> OTHER INFORMATION: Xaa = Gln, Ala, Orn, Nle or Lys
<220> FEATURE:
<221> NAME/KEY: VARIANT
```

```
<222> LOCATION: (5)..(5)
<223> OTHER INFORMATION: Xaa = Arg, Ala or Lys
<220> FEATURE:
<221> NAME/KEY: VARIANT
<222> LOCATION: (6)..(6)
<223> OTHER INFORMATION: Xaa = Asn, Ala, Orn or Nle
<220> FEATURE:
<221> NAME/KEY: VARIANT
<222> LOCATION: (7)..(7)
<223> OTHER INFORMATION: Xaa = Met, Ala or Leu
<220> FEATURE:
<221> NAME/KEY: VARIANT
<222> LOCATION: (8)..(8)
<223> OTHER INFORMATION: Xaa = Arg, Ala or Lys

<400> SEQUENCE: 1

Phe Xaa Xaa Xaa Xaa Xaa Xaa Xaa Lys Val Arg
1               5                   10


<210> SEQ ID NO 2
<211> LENGTH: 19
<212> TYPE: PRT
<213> ORGANISM: Artificial
<220> FEATURE:
<223> OTHER INFORMATION: Sequence derived from human lactoferrin

<400> SEQUENCE: 2

Gly Arg Arg Arg Arg Ser Val Gln Trp Cys Ala Val Ser Gln Pro Glu
1               5                   10                  15

Ala Thr Lys


<210> SEQ ID NO 3
<211> LENGTH: 9
<212> TYPE: PRT
<213> ORGANISM: Artificial
<220> FEATURE:
<223> OTHER INFORMATION: Sequence derived from human lactoferrin

<400> SEQUENCE: 3

Gly Pro Pro Val Ser Cys Ile Lys Arg
1               5


<210> SEQ ID NO 4
<211> LENGTH: 25
<212> TYPE: PRT
<213> ORGANISM: Artificial
<220> FEATURE:
<223> OTHER INFORMATION: Sequence derived from human lactoferrin
<220> FEATURE:
<221> NAME/KEY: VARIANT
<222> LOCATION: (1)..(1)
<223> OTHER INFORMATION: Acetylation
<220> FEATURE:
<221> NAME/KEY: VARIANT
<222> LOCATION: (25)..(25)
<223> OTHER INFORMATION: Amidation

<400> SEQUENCE: 4

Glu Ala Thr Lys Cys Phe Gln Trp Gln Arg Asn Met Arg Lys Val Arg
1               5                   10                  15

Gly Pro Pro Val Ser Cys Ile Lys Arg
            20                  25


<210> SEQ ID NO 5
<211> LENGTH: 23
<212> TYPE: PRT
<213> ORGANISM: Artificial
<220> FEATURE:
<223> OTHER INFORMATION: Sequence derived from human lactoferrin
```

-continued

```
<400> SEQUENCE: 5

Thr Lys Cys Phe Gln Trp Gln Arg Asn Met Arg Lys Val Arg Gly Pro
1               5                   10                  15

Pro Val Ser Cys Ile Lys Arg
            20


<210> SEQ ID NO 6
<211> LENGTH: 20
<212> TYPE: PRT
<213> ORGANISM: Artificial
<220> FEATURE:
<223> OTHER INFORMATION: Sequence derived from human lactoferrin

<400> SEQUENCE: 6

Val Ser Gln Pro Glu Ala Thr Lys Cys Phe Gln Trp Gln Arg Asn Met
1               5                   10                  15

Arg Lys Val Arg
            20


<210> SEQ ID NO 7
<211> LENGTH: 16
<212> TYPE: PRT
<213> ORGANISM: Artificial
<220> FEATURE:
<223> OTHER INFORMATION: Sequence derived from human lactoferrin

<400> SEQUENCE: 7

Glu Ala Thr Lys Cys Phe Gln Trp Gln Arg Asn Met Arg Lys Val Arg
1               5                   10                  15


<210> SEQ ID NO 8
<211> LENGTH: 19
<212> TYPE: PRT
<213> ORGANISM: Artificial
<220> FEATURE:
<223> OTHER INFORMATION: Sequence derived from human lactoferrin

<400> SEQUENCE: 8

Ser Gln Pro Glu Ala Thr Lys Cys Phe Gln Trp Gln Arg Asn Met Arg
1               5                   10                  15

Lys Val Arg


<210> SEQ ID NO 9
<211> LENGTH: 18
<212> TYPE: PRT
<213> ORGANISM: Artificial
<220> FEATURE:
<223> OTHER INFORMATION: Sequence derived from human lactoferrin

<400> SEQUENCE: 9

Gln Pro Glu Ala Thr Lys Cys Phe Gln Trp Gln Arg Asn Met Arg Lys
1               5                   10                  15

Val Arg


<210> SEQ ID NO 10
<211> LENGTH: 15
<212> TYPE: PRT
<213> ORGANISM: Artificial
<220> FEATURE:
<223> OTHER INFORMATION: Sequence derived from human lactoferrin

<400> SEQUENCE: 10

Ala Thr Lys Cys Phe Gln Trp Gln Arg Asn Met Arg Lys Val Arg
```

-continued 1 5 10 15

<210> SEQ ID NO 11
<211> LENGTH: 14
<212> TYPE: PRT
<213> ORGANISM: Artificial
<220> FEATURE:
<223> OTHER INFORMATION: Sequence derived from human lactoferrin

<400> SEQUENCE: 11

Thr Lys Cys Phe Gln Trp Gln Arg Asn Met Arg Lys Val Arg
1 5 10

<210> SEQ ID NO 12
<211> LENGTH: 13
<212> TYPE: PRT
<213> ORGANISM: Artificial
<220> FEATURE:
<223> OTHER INFORMATION: Sequence derived from human lactoferrin

<400> SEQUENCE: 12

Lys Cys Phe Gln Trp Gln Arg Asn Met Arg Lys Val Arg
1 5 10

<210> SEQ ID NO 13
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 13

Cys Phe Gln Trp Gln Arg Asn Met Arg Lys Val Arg
1 5 10

<210> SEQ ID NO 14
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 14

Cys Phe Ala Trp Gln Arg Asn Met Arg Lys Val Arg
1 5 10

<210> SEQ ID NO 15
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 15

Cys Phe Gln Trp Ala Arg Asn Met Arg Lys Val Arg
1 5 10

<210> SEQ ID NO 16
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 16

Cys Phe Gln Trp Gln Ala Asn Met Arg Lys Val Arg
1 5 10

-continued

<210> SEQ ID NO 17
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 17

Cys Phe Gln Trp Gln Arg Ala Met Arg Lys Val Arg
1 5 10

<210> SEQ ID NO 18
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 18

Cys Phe Gln Trp Gln Arg Asn Ala Arg Lys Val Arg
1 5 10

<210> SEQ ID NO 19
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 19

Cys Phe Gln Trp Gln Arg Asn Met Ala Lys Val Arg
1 5 10

<210> SEQ ID NO 20
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 20

Cys Phe Gln Leu Gln Arg Asn Met Arg Lys Val Arg
1 5 10

<210> SEQ ID NO 21
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 21

Cys Phe Gln Trp Gln Lys Asn Met Arg Lys Val Arg
1 5 10

<210> SEQ ID NO 22
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 22

Cys Phe Gln Trp Gln Arg Asn Leu Arg Lys Val Arg
1 5 10

<210> SEQ ID NO 23
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 23

Cys Phe Gln Trp Gln Arg Asn Met Arg Arg Val Arg
1 5 10

<210> SEQ ID NO 24
<211> LENGTH: 12
<212> TYPE: PRT
<213> ORGANISM: Artificial
<220> FEATURE:
<223> OTHER INFORMATION: Sequence derived from human lactoferrin
<220> FEATURE:
<221> NAME/KEY: Variant
<222> LOCATION: (5)..(5)
<223> OTHER INFORMATION: Xaa = Orn

<400> SEQUENCE: 24

Cys Phe Gln Trp Xaa Arg Asn Met Arg Lys Val Arg
1 5 10

<210> SEQ ID NO 25
<211> LENGTH: 12
<212> TYPE: PRT
<213> ORGANISM: Artificial
<220> FEATURE:
<223> OTHER INFORMATION: Sequence derived from human lactoferrin
<220> FEATURE:
<221> NAME/KEY: Variant
<222> LOCATION: (5)..(5)
<223> OTHER INFORMATION: Xaa = Nle

<400> SEQUENCE: 25

Cys Phe Gln Trp Xaa Arg Asn Met Arg Lys Val Arg
1 5 10

<210> SEQ ID NO 26
<211> LENGTH: 12
<212> TYPE: PRT
<213> ORGANISM: Artificial
<220> FEATURE:
<223> OTHER INFORMATION: Sequence derived from human lactoferrin
<220> FEATURE:
<221> NAME/KEY: Variant
<222> LOCATION: (7)..(7)
<223> OTHER INFORMATION: Xaa = Orn

<400> SEQUENCE: 26

Cys Phe Gln Trp Gln Arg Xaa Met Arg Lys Val Arg
1 5 10

<210> SEQ ID NO 27
<211> LENGTH: 12
<212> TYPE: PRT
<213> ORGANISM: Artificial
<220> FEATURE:
<223> OTHER INFORMATION: Sequence derived from human lactoferrin
<220> FEATURE:
<221> NAME/KEY: Variant
<222> LOCATION: (7)..(7)
<223> OTHER INFORMATION: Xaa = Nle

<400> SEQUENCE: 27

Cys Phe Gln Trp Gln Arg Xaa Met Arg Lys Val Arg

-continued

```
1               5                   10


<210> SEQ ID NO 28
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 28

Cys Phe Gln Trp Lys Arg Asn Met Arg Lys Val Arg
1               5                   10


<210> SEQ ID NO 29
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 29

Cys Phe Gln Trp Lys Arg Ala Met Arg Lys Val Arg
1               5                   10


<210> SEQ ID NO 30
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 30

Cys Phe Ala Trp Lys Arg Asn Met Arg Lys Val Arg
1               5                   10


<210> SEQ ID NO 31
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 31

Cys Phe Ala Trp Gln Arg Ala Met Arg Lys Val Arg
1               5                   10


<210> SEQ ID NO 32
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 32

Cys Phe Gln Leu Gln Lys Asn Met Lys Lys Val Arg
1               5                   10


<210> SEQ ID NO 33
<211> LENGTH: 12
<212> TYPE: PRT
<213> ORGANISM: Artificial
<220> FEATURE:
<223> OTHER INFORMATION: Sequence derived from human lactoferrin

<400> SEQUENCE: 33

Cys Phe Ala Leu Lys Lys Ala Met Lys Lys Val Arg
1               5                   10
```

```
<210> SEQ ID NO 34
<211> LENGTH: 25
<212> TYPE: PRT
<213> ORGANISM: Artificial
<220> FEATURE:
<223> OTHER INFORMATION: Sequence derived from human lactoferrin

<400> SEQUENCE: 34

Glu Ala Thr Lys Cys Phe Gln Trp Lys Arg Asn Met Arg Lys Val Arg
1               5                   10                  15

Gly Pro Pro Val Ser Cys Ile Lys Arg
            20                  25


<210> SEQ ID NO 35
<211> LENGTH: 24
<212> TYPE: PRT
<213> ORGANISM: Artificial
<220> FEATURE:
<223> OTHER INFORMATION: Sequence derived from human lactoferrin

<400> SEQUENCE: 35

Ala Thr Lys Cys Phe Gln Trp Lys Arg Asn Met Arg Lys Val Arg Gly
1               5                   10                  15

Pro Pro Val Ser Cys Ile Lys Arg
            20


<210> SEQ ID NO 36
<211> LENGTH: 23
<212> TYPE: PRT
<213> ORGANISM: Artificial
<220> FEATURE:
<223> OTHER INFORMATION: Sequence derived from human lactoferrin

<400> SEQUENCE: 36

Thr Lys Cys Phe Gln Trp Lys Arg Asn Met Arg Lys Val Arg Gly Pro
1               5                   10                  15

Pro Val Ser Cys Ile Lys Arg
            20


<210> SEQ ID NO 37
<211> LENGTH: 22
<212> TYPE: PRT
<213> ORGANISM: Artificial
<220> FEATURE:
<223> OTHER INFORMATION: Sequence derived from human lactoferrin

<400> SEQUENCE: 37

Lys Cys Phe Gln Trp Lys Arg Asn Met Arg Lys Val Arg Gly Pro Pro
1               5                   10                  15

Val Ser Cys Ile Lys Arg
            20


<210> SEQ ID NO 38
<211> LENGTH: 24
<212> TYPE: PRT
<213> ORGANISM: Artificial
<220> FEATURE:
<223> OTHER INFORMATION: Sequence derived from human lactoferrin

<400> SEQUENCE: 38

Glu Ala Thr Lys Cys Phe Gln Trp Lys Arg Asn Met Arg Lys Val Arg
1               5                   10                  15

Gly Pro Pro Val Ser Cys Ile Lys
```

-continued

20

<210> SEQ ID NO 39
<211> LENGTH: 23
<212> TYPE: PRT
<213> ORGANISM: Artificial
<220> FEATURE:
<223> OTHER INFORMATION: Sequence derived from human lactoferrin

<400> SEQUENCE: 39

Glu Ala Thr Lys Cys Phe Gln Trp Lys Arg Asn Met Arg Lys Val Arg
1 5 10 15

Gly Pro Pro Val Ser Cys Ile
20

<210> SEQ ID NO 40
<211> LENGTH: 22
<212> TYPE: PRT
<213> ORGANISM: Artificial
<220> FEATURE:
<223> OTHER INFORMATION: Sequence derived from human lactoferrin

<400> SEQUENCE: 40

Glu Ala Thr Lys Cys Phe Gln Trp Lys Arg Asn Met Arg Lys Val Arg
1 5 10 15

Gly Pro Pro Val Ser Cys
20

<210> SEQ ID NO 41
<211> LENGTH: 25
<212> TYPE: PRT
<213> ORGANISM: Artificial
<220> FEATURE:
<223> OTHER INFORMATION: Sequence derived from human lactoferrin

<400> SEQUENCE: 41

Glu Ala Thr Lys Cys Phe Gln Trp Lys Arg Ala Met Arg Lys Val Arg
1 5 10 15

Gly Pro Pro Val Ser Cys Ile Lys Arg
20 25

<210> SEQ ID NO 42
<211> LENGTH: 24
<212> TYPE: PRT
<213> ORGANISM: Artificial
<220> FEATURE:
<223> OTHER INFORMATION: Sequence derived from human lactoferrin

<400> SEQUENCE: 42

Ala Thr Lys Cys Phe Gln Trp Lys Arg Ala Met Arg Lys Val Arg Gly
1 5 10 15

Pro Pro Val Ser Cys Ile Lys Arg
20

<210> SEQ ID NO 43
<211> LENGTH: 23
<212> TYPE: PRT
<213> ORGANISM: Artificial
<220> FEATURE:
<223> OTHER INFORMATION: Sequence derived from human lactoferrin

<400> SEQUENCE: 43

Thr Lys Cys Phe Gln Trp Lys Arg Ala Met Arg Lys Val Arg Gly Pro
1 5 10 15

Pro Val Ser Cys Ile Lys Arg
20

<210> SEQ ID NO 44
<211> LENGTH: 22
<212> TYPE: PRT
<213> ORGANISM: Artificial
<220> FEATURE:
<223> OTHER INFORMATION: Sequence derived from human lactoferrin

<400> SEQUENCE: 44

Lys Cys Phe Gln Trp Lys Arg Ala Met Arg Lys Val Arg Gly Pro Pro
1 5 10 15

Val Ser Cys Ile Lys Arg
20

<210> SEQ ID NO 45
<211> LENGTH: 24
<212> TYPE: PRT
<213> ORGANISM: Artificial
<220> FEATURE:
<223> OTHER INFORMATION: Sequence derived from human lactoferrin

<400> SEQUENCE: 45

Glu Ala Thr Lys Cys Phe Gln Trp Lys Arg Ala Met Arg Lys Val Arg
1 5 10 15

Gly Pro Pro Val Ser Cys Ile Lys
20

<210> SEQ ID NO 46
<211> LENGTH: 23
<212> TYPE: PRT
<213> ORGANISM: Artificial
<220> FEATURE:
<223> OTHER INFORMATION: Sequence derived from human lactoferrin

<400> SEQUENCE: 46

Glu Ala Thr Lys Cys Phe Gln Trp Lys Arg Ala Met Arg Lys Val Arg
1 5 10 15

Gly Pro Pro Val Ser Cys Ile
20

<210> SEQ ID NO 47
<211> LENGTH: 22
<212> TYPE: PRT
<213> ORGANISM: Artificial
<220> FEATURE:
<223> OTHER INFORMATION: Sequence derived from human lactoferrin

<400> SEQUENCE: 47

Glu Ala Thr Lys Cys Phe Gln Trp Lys Arg Ala Met Arg Lys Val Arg
1 5 10 15

Gly Pro Pro Val Ser Cys
20

<210> SEQ ID NO 48
<211> LENGTH: 20
<212> TYPE: PRT
<213> ORGANISM: Artificial
<220> FEATURE:
<223> OTHER INFORMATION: Sequence derived from human lactoferrin

<400> SEQUENCE: 48

Gly Arg Arg Arg Arg Ser Val Gln Trp Cys Ala Val Ser Gln Pro Glu
1 5 10 15

Ala Thr Lys Cys
20

<210> SEQ ID NO 49
<211> LENGTH: 8
<212> TYPE: PRT
<213> ORGANISM: Artificial
<220> FEATURE:
<223> OTHER INFORMATION: Sequence derived from human lactoferrin

<400> SEQUENCE: 49

Pro Pro Val Ser Cys Ile Lys Arg
1 5

<210> SEQ ID NO 50
<211> LENGTH: 18
<212> TYPE: PRT
<213> ORGANISM: Artificial
<220> FEATURE:
<223> OTHER INFORMATION: Sequence derived from human lactoferrin
<220> FEATURE:
<221> NAME/KEY: VARIANT
<222> LOCATION: (1)..(1)
<223> OTHER INFORMATION: Acetylation
<220> FEATURE:
<221> NAME/KEY: VARIANT
<222> LOCATION: (18)..(18)
<223> OTHER INFORMATION: Amidation

<400> SEQUENCE: 50

Phe Gln Trp Gln Arg Asn Met Arg Lys Val Arg Gly Ser Arg Arg Arg
1 5 10 15

Arg Gly

<210> SEQ ID NO 51
<211> LENGTH: 22
<212> TYPE: PRT
<213> ORGANISM: Artificial
<220> FEATURE:
<223> OTHER INFORMATION: Sequence derived from human lactoferrin
<220> FEATURE:
<221> NAME/KEY: Variant
<222> LOCATION: (4)..(4)
<223> OTHER INFORMATION: Cys modified to acetamidomethyl-Cys
<220> FEATURE:
<221> NAME/KEY: Variant
<222> LOCATION: (22)..(22)
<223> OTHER INFORMATION: Amidation

<400> SEQUENCE: 51

Ala Thr Lys Cys Phe Gln Trp Gln Arg Asn Met Arg Lys Val Arg Gly
1 5 10 15

Ser Arg Arg Arg Arg Gly
20

<210> SEQ ID NO 52
<211> LENGTH: 18
<212> TYPE: PRT
<213> ORGANISM: Artificial
<220> FEATURE:
<223> OTHER INFORMATION: Sequence derived from human lactoferrin
<220> FEATURE:
<221> NAME/KEY: VARIANT
<222> LOCATION: (1)..(1)
<223> OTHER INFORMATION: Acetylation
<220> FEATURE:
<221> NAME/KEY: VARIANT
<222> LOCATION: (18)..(18)
<223> OTHER INFORMATION: Amidation

<400> SEQUENCE: 52

Phe Gln Trp Lys Arg Asn Met Arg Lys Val Arg Gly Ser Arg Arg Arg
1               5                   10                  15

Arg Gly

<210> SEQ ID NO 53
<211> LENGTH: 22
<212> TYPE: PRT
<213> ORGANISM: Artificial
<220> FEATURE:
<223> OTHER INFORMATION: Sequence derived from human lactoferrin
<220> FEATURE:
<221> NAME/KEY: Variant
<222> LOCATION: (4)..(4)
<223> OTHER INFORMATION: Cys modified to acetamidomethyl-Cys
<220> FEATURE:
<221> NAME/KEY: Variant
<222> LOCATION: (22)..(22)
<223> OTHER INFORMATION: Acetylation

<400> SEQUENCE: 53

Ala Thr Lys Cys Phe Gln Trp Lys Arg Asn Met Arg Lys Val Arg Gly
1               5                   10                  15

Ser Arg Arg Arg Arg Gly
            20

<210> SEQ ID NO 54
<211> LENGTH: 18
<212> TYPE: PRT
<213> ORGANISM: Artificial
<220> FEATURE:
<223> OTHER INFORMATION: Sequence derived from human lactoferrin
<220> FEATURE:
<221> NAME/KEY: VARIANT
<222> LOCATION: (1)..(1)
<223> OTHER INFORMATION: Acetylation
<220> FEATURE:
<221> NAME/KEY: VARIANT
<222> LOCATION: (18)..(18)
<223> OTHER INFORMATION: Amidation

<400> SEQUENCE: 54

Phe Gln Trp Lys Arg Ala Met Arg Lys Val Arg Gly Ser Arg Arg Arg
1               5                   10                  15

Arg Gly

<210> SEQ ID NO 55
<211> LENGTH: 22
<212> TYPE: PRT
<213> ORGANISM: Artificial
<220> FEATURE:
<223> OTHER INFORMATION: Sequence derived from human lactoferrin
<220> FEATURE:
<221> NAME/KEY: Variant
<222> LOCATION: (4)..(4)
<223> OTHER INFORMATION: Cys modified to acetamidomethyl-Cys
<220> FEATURE:
<221> NAME/KEY: Variant
<222> LOCATION: (22)..(22)
<223> OTHER INFORMATION: Amidation

<400> SEQUENCE: 55

Ala Thr Lys Cys Phe Gln Trp Lys Arg Ala Met Arg Lys Val Arg Gly
1               5                   10                  15

Ser Arg Arg Arg Arg Gly
            20

-continued

<210> SEQ ID NO 56
<211> LENGTH: 25
<212> TYPE: PRT
<213> ORGANISM: Artificial
<220> FEATURE:
<223> OTHER INFORMATION: Sequence derived from human lactoferrin
<220> FEATURE:
<221> NAME/KEY: VARIANT
<222> LOCATION: (1)..(1)
<223> OTHER INFORMATION: Acetylation
<220> FEATURE:
<221> NAME/KEY: DISULFID
<222> LOCATION: (5)..(22)
<220> FEATURE:
<221> NAME/KEY: VARIANT
<222> LOCATION: (25)..(25)
<223> OTHER INFORMATION: Amidation

<400> SEQUENCE: 56

```
Glu Ala Thr Lys Cys Phe Gln Trp Gln Arg Asn Met Arg Lys Val Arg
1               5                   10                  15

Gly Pro Pro Val Ser Cys Ile Lys Arg
            20                  25
```

<210> SEQ ID NO 57
<211> LENGTH: 18
<212> TYPE: PRT
<213> ORGANISM: artificial
<220> FEATURE:
<223> OTHER INFORMATION: Sequence derived from human lactoferrin

<400> SEQUENCE: 57

```
Arg Arg Arg Arg Ser Val Gln Trp Cys Ala Val Ser Gln Pro Glu Ala
1               5                   10                  15

Thr Lys
```

<210> SEQ ID NO 58
<211> LENGTH: 17
<212> TYPE: PRT
<213> ORGANISM: artificial
<220> FEATURE:
<223> OTHER INFORMATION: Sequence derived from human lactoferrin

<400> SEQUENCE: 58

```
Arg Arg Arg Ser Val Gln Trp Cys Ala Val Ser Gln Pro Glu Ala Thr
1               5                   10                  15

Lys
```

<210> SEQ ID NO 59
<211> LENGTH: 16
<212> TYPE: PRT
<213> ORGANISM: artificial
<220> FEATURE:
<223> OTHER INFORMATION: Sequence derived from human lactoferrin

<400> SEQUENCE: 59

```
Arg Arg Ser Val Gln Trp Cys Ala Val Ser Gln Pro Glu Ala Thr Lys
1               5                   10                  15
```

<210> SEQ ID NO 60
<211> LENGTH: 15
<212> TYPE: PRT
<213> ORGANISM: artificial
<220> FEATURE:
<223> OTHER INFORMATION: Sequence derived from human lactoferrin

<400> SEQUENCE: 60

Arg Ser Val Gln Trp Cys Ala Val Ser Gln Pro Glu Ala Thr Lys
1 5 10 15

<210> SEQ ID NO 61
<211> LENGTH: 14
<212> TYPE: PRT
<213> ORGANISM: artificial
<220> FEATURE:
<223> OTHER INFORMATION: Sequence derived from human lactoferrin

<400> SEQUENCE: 61

Ser Val Gln Trp Cys Ala Val Ser Gln Pro Glu Ala Thr Lys
1 5 10

<210> SEQ ID NO 62
<211> LENGTH: 13
<212> TYPE: PRT
<213> ORGANISM: artificial
<220> FEATURE:
<223> OTHER INFORMATION: Sequence derived from human lactoferrin

<400> SEQUENCE: 62

Val Gln Trp Cys Ala Val Ser Gln Pro Glu Ala Thr Lys
1 5 10

<210> SEQ ID NO 63
<211> LENGTH: 12
<212> TYPE: PRT
<213> ORGANISM: artificial
<220> FEATURE:
<223> OTHER INFORMATION: Sequence derived from human lactoferrin

<400> SEQUENCE: 63

Gln Trp Cys Ala Val Ser Gln Pro Glu Ala Thr Lys
1 5 10

<210> SEQ ID NO 64
<211> LENGTH: 11
<212> TYPE: PRT
<213> ORGANISM: artificial
<220> FEATURE:
<223> OTHER INFORMATION: Sequence derived from human lactoferrin

<400> SEQUENCE: 64

Trp Cys Ala Val Ser Gln Pro Glu Ala Thr Lys
1 5 10

<210> SEQ ID NO 65
<211> LENGTH: 10
<212> TYPE: PRT
<213> ORGANISM: artificial
<220> FEATURE:
<223> OTHER INFORMATION: Sequence derived from human lactoferrin

<400> SEQUENCE: 65

Cys Ala Val Ser Gln Pro Glu Ala Thr Lys
1 5 10

<210> SEQ ID NO 66
<211> LENGTH: 9
<212> TYPE: PRT
<213> ORGANISM: artificial
<220> FEATURE:
<223> OTHER INFORMATION: Sequence derived from human lactoferrin

<400> SEQUENCE: 66

Ala Val Ser Gln Pro Glu Ala Thr Lys
1               5

<210> SEQ ID NO 67
<211> LENGTH: 8
<212> TYPE: PRT
<213> ORGANISM: artificial
<220> FEATURE:
<223> OTHER INFORMATION: Sequence derived from human lactoferrin

<400> SEQUENCE: 67

Val Ser Gln Pro Glu Ala Thr Lys
1               5

<210> SEQ ID NO 68
<211> LENGTH: 7
<212> TYPE: PRT
<213> ORGANISM: artificial
<220> FEATURE:
<223> OTHER INFORMATION: Sequence derived from human lactoferrin

<400> SEQUENCE: 68

Ser Gln Pro Glu Ala Thr Lys
1               5

<210> SEQ ID NO 69
<211> LENGTH: 6
<212> TYPE: PRT
<213> ORGANISM: artificial
<220> FEATURE:
<223> OTHER INFORMATION: Sequence derived from human lactoferrin

<400> SEQUENCE: 69

Gln Pro Glu Ala Thr Lys
1               5

<210> SEQ ID NO 70
<211> LENGTH: 5
<212> TYPE: PRT
<213> ORGANISM: artificial
<220> FEATURE:
<223> OTHER INFORMATION: Sequence derived from human lactoferrin

<400> SEQUENCE: 70

Pro Glu Ala Thr Lys
1               5

<210> SEQ ID NO 71
<211> LENGTH: 4
<212> TYPE: PRT
<213> ORGANISM: artificial
<220> FEATURE:
<223> OTHER INFORMATION: Sequence derived from human lactoferrin

<400> SEQUENCE: 71

Glu Ala Thr Lys
1

<210> SEQ ID NO 72
<211> LENGTH: 8
<212> TYPE: PRT
<213> ORGANISM: artificial
<220> FEATURE:
<223> OTHER INFORMATION: Sequence derived from human lactoferrin

<400> SEQUENCE: 72

Gly Pro Pro Val Ser Cys Ile Lys 1 5

<210> SEQ ID NO 73
<211> LENGTH: 7
<212> TYPE: PRT
<213> ORGANISM: artificial
<220> FEATURE:
<223> OTHER INFORMATION: Sequence derived from human lactoferrin

<400> SEQUENCE: 73

Gly Pro Pro Val Ser Cys Ile
1 5

<210> SEQ ID NO 74
<211> LENGTH: 6
<212> TYPE: PRT
<213> ORGANISM: artificial
<220> FEATURE:
<223> OTHER INFORMATION: Sequence derived from human lactoferrin

<400> SEQUENCE: 74

Gly Pro Pro Val Ser Cys
1 5

<210> SEQ ID NO 75
<211> LENGTH: 5
<212> TYPE: PRT
<213> ORGANISM: artificial
<220> FEATURE:
<223> OTHER INFORMATION: Sequence derived from human lactoferrin

<400> SEQUENCE: 75

Gly Pro Pro Val Ser
1 5

<210> SEQ ID NO 76
<211> LENGTH: 4
<212> TYPE: PRT
<213> ORGANISM: artificial
<220> FEATURE:
<223> OTHER INFORMATION: Sequence derived from human lactoferrind

<400> SEQUENCE: 76

Gly Pro Pro Val
1

<210> SEQ ID NO 77
<211> LENGTH: 19
<212> TYPE: PRT
<213> ORGANISM: artificial
<220> FEATURE:
<223> OTHER INFORMATION: Sequence derived from human lactoferrin

<400> SEQUENCE: 77

Gly Arg Arg Arg Arg Ser Val Gln Trp Cys Ala Val Ser Gln Pro Glu
1 5 10 15

Ala Thr Lys

<210> SEQ ID NO 78
<211> LENGTH: 19
<212> TYPE: PRT
<213> ORGANISM: artificial
<220> FEATURE:
<223> OTHER INFORMATION: Sequence derived from human lactoferrin

<400> SEQUENCE: 78

-continued

```
Arg Arg Arg Arg Ser Val Gln Trp Cys Ala Val Ser Gln Pro Glu Ala
1               5                   10                  15

Thr Lys Cys


<210> SEQ ID NO 79
<211> LENGTH: 18
<212> TYPE: PRT
<213> ORGANISM: artificial
<220> FEATURE:
<223> OTHER INFORMATION: Sequence derived from human lactoferrin

<400> SEQUENCE: 79

Arg Arg Arg Ser Val Gln Trp Cys Ala Val Ser Gln Pro Glu Ala Thr
1               5                   10                  15

Lys Cys


<210> SEQ ID NO 80
<211> LENGTH: 17
<212> TYPE: PRT
<213> ORGANISM: artificial
<220> FEATURE:
<223> OTHER INFORMATION: Sequence derived from human lactoferrin

<400> SEQUENCE: 80

Arg Arg Ser Val Gln Trp Cys Ala Val Ser Gln Pro Glu Ala Thr Lys
1               5                   10                  15

Cys


<210> SEQ ID NO 81
<211> LENGTH: 16
<212> TYPE: PRT
<213> ORGANISM: artificial
<220> FEATURE:
<223> OTHER INFORMATION: Sequence derived from human lactoferrin

<400> SEQUENCE: 81

Arg Ser Val Gln Trp Cys Ala Val Ser Gln Pro Glu Ala Thr Lys Cys
1               5                   10                  15


<210> SEQ ID NO 82
<211> LENGTH: 14
<212> TYPE: PRT
<213> ORGANISM: artificial
<220> FEATURE:
<223> OTHER INFORMATION: Sequence derived from human lactoferrin

<400> SEQUENCE: 82

Ser Val Gln Trp Cys Ala Val Ser Gln Pro Glu Ala Thr Lys
1               5                   10


<210> SEQ ID NO 83
<211> LENGTH: 13
<212> TYPE: PRT
<213> ORGANISM: artificial
<220> FEATURE:
<223> OTHER INFORMATION: Sequence derived from human lactoferrin

<400> SEQUENCE: 83

Val Gln Trp Cys Ala Val Ser Gln Pro Glu Ala Thr Lys
1               5                   10


<210> SEQ ID NO 84
<211> LENGTH: 13
<212> TYPE: PRT
<213> ORGANISM: artificial
```

<220> FEATURE:
<223> OTHER INFORMATION: Sequence derived from human lactoferrin

<400> SEQUENCE: 84

Gln Trp Cys Ala Val Ser Gln Pro Glu Ala Thr Lys Cys
1 5 10

<210> SEQ ID NO 85
<211> LENGTH: 12
<212> TYPE: PRT
<213> ORGANISM: artificial
<220> FEATURE:
<223> OTHER INFORMATION: Sequence derived from human lactoferrin

<400> SEQUENCE: 85

Trp Cys Ala Val Ser Gln Pro Glu Ala Thr Lys Cys
1 5 10

<210> SEQ ID NO 86
<211> LENGTH: 11
<212> TYPE: PRT
<213> ORGANISM: artificial
<220> FEATURE:
<223> OTHER INFORMATION: Sequence derived from human lactoferrin

<400> SEQUENCE: 86

Cys Ala Val Ser Gln Pro Glu Ala Thr Lys Cys
1 5 10

<210> SEQ ID NO 87
<211> LENGTH: 10
<212> TYPE: PRT
<213> ORGANISM: artificial
<220> FEATURE:
<223> OTHER INFORMATION: Sequence derived from human lactoferrin

<400> SEQUENCE: 87

Ala Val Ser Gln Pro Glu Ala Thr Lys Cys
1 5 10

<210> SEQ ID NO 88
<211> LENGTH: 9
<212> TYPE: PRT
<213> ORGANISM: artificial
<220> FEATURE:
<223> OTHER INFORMATION: Sequence derived from human lactoferrin

<400> SEQUENCE: 88

Val Ser Gln Pro Glu Ala Thr Lys Cys
1 5

<210> SEQ ID NO 89
<211> LENGTH: 8
<212> TYPE: PRT
<213> ORGANISM: artificial
<220> FEATURE:
<223> OTHER INFORMATION: Sequence derived from human lactoferrin

<400> SEQUENCE: 89

Ser Gln Pro Glu Ala Thr Lys Cys
1 5

<210> SEQ ID NO 90
<211> LENGTH: 7
<212> TYPE: PRT
<213> ORGANISM: artificial
<220> FEATURE:

<223> OTHER INFORMATION: Sequence derived from human lactoferrin

<400> SEQUENCE: 90

Gln Pro Glu Ala Thr Lys Cys
1 5

<210> SEQ ID NO 91
<211> LENGTH: 6
<212> TYPE: PRT
<213> ORGANISM: artificial
<220> FEATURE:
<223> OTHER INFORMATION: Sequence derived from human lactoferrin

<400> SEQUENCE: 91

Pro Glu Ala Thr Lys Cys
1 5

<210> SEQ ID NO 92
<211> LENGTH: 5
<212> TYPE: PRT
<213> ORGANISM: artificial
<220> FEATURE:
<223> OTHER INFORMATION: Sequence derived from human lactoferrin

<400> SEQUENCE: 92

Glu Ala Thr Lys Cys
1 5

<210> SEQ ID NO 93
<211> LENGTH: 4
<212> TYPE: PRT
<213> ORGANISM: artificial
<220> FEATURE:
<223> OTHER INFORMATION: Sequence derived from human lactoferrin

<400> SEQUENCE: 93

Ala Thr Lys Cys
1

<210> SEQ ID NO 94
<211> LENGTH: 7
<212> TYPE: PRT
<213> ORGANISM: artificial
<220> FEATURE:
<223> OTHER INFORMATION: Sequence derived from human lactoferrin

<400> SEQUENCE: 94

Pro Pro Val Ser Cys Ile Lys
1 5

<210> SEQ ID NO 95
<211> LENGTH: 6
<212> TYPE: PRT
<213> ORGANISM: artificial
<220> FEATURE:
<223> OTHER INFORMATION: Sequence derived from human lactoferrin

<400> SEQUENCE: 95

Pro Pro Val Ser Cys Ile
1 5

<210> SEQ ID NO 96
<211> LENGTH: 5
<212> TYPE: PRT
<213> ORGANISM: artificial
<220> FEATURE:
<223> OTHER INFORMATION: Sequence derived from human lactoferrin -continued

```
<400> SEQUENCE: 96

Pro Pro Val Ser Cys
1               5


<210> SEQ ID NO 97
<211> LENGTH: 4
<212> TYPE: PRT
<213> ORGANISM: artificial
<220> FEATURE:
<223> OTHER INFORMATION: Sequence derived from human lactoferrin

<400> SEQUENCE: 97

Pro Pro Val Ser
1
```